US011441146B2

(12) United States Patent
Kmiec et al.

(10) Patent No.: US 11,441,146 B2
(45) Date of Patent: Sep. 13, 2022

(54) COMPOSITIONS AND METHODS FOR IMPROVING HOMOGENEITY OF DNA GENERATED USING A CRISPR/CAS9 CLEAVAGE SYSTEM

(71) Applicant: Christiana Care Health Services, Inc., Newark, DE (US)

(72) Inventors: Eric Brian Kmiec, Middletown, DE (US); Pawel Alexander Bialk, Wilmington, DE (US)

(73) Assignee: Christiana Care Health Services, Inc., Newark, DE (US)

( * ) Notice: Subject to any disclaimer, the term of this patent is extended or adjusted under 35 U.S.C. 154(b) by 72 days.

(21) Appl. No.: 15/402,833

(22) Filed: Jan. 10, 2017

(65) Prior Publication Data

US 2017/0198277 A1 Jul. 13, 2017

Related U.S. Application Data

(60) Provisional application No. 62/442,145, filed on Jan. 4, 2017, provisional application No. 62/277,212, filed on Jan. 11, 2016.

(51) Int. Cl.
| | | |
|---|---|---|
| *C12Q 1/68* | (2018.01) | |
| *C12N 15/10* | (2006.01) | |
| *C12N 9/22* | (2006.01) | |
| *C12N 15/90* | (2006.01) | |

(52) U.S. Cl.
CPC ............ *C12N 15/102* (2013.01); *C12N 9/22* (2013.01); *C12N 15/90* (2013.01)

(58) Field of Classification Search
None
See application file for complete search history.

(56) References Cited

U.S. PATENT DOCUMENTS

| | | | |
|---|---|---|---|
| 5,399,346 | A | 3/1995 | Anderson |
| 5,580,859 | A | 12/1996 | Felgner |
| 5,589,466 | A | 12/1996 | Felgner |
| 6,326,193 | B1 | 12/2001 | Liu |
| 2011/0059502 | A1 | 3/2011 | Chalasani |
| 2014/0068797 | A1 | 3/2014 | Doudna |
| 2016/0369301 | A1* | 12/2016 | Church .................. C12N 15/85 |
| 2017/0015994 | A1* | 1/2017 | Anderson ............ A61K 31/713 |

FOREIGN PATENT DOCUMENTS

| | | |
|---|---|---|
| WO | 0129058 | 4/2001 |
| WO | 0196584 | 12/2001 |

OTHER PUBLICATIONS

Lin et al (eLIFE 2014, 3: e04766,pp. 1-13).*
Anderson, WF., "Human Gene Therapy," Science, May 8, 1992, vol. 256, Issue 5058, pp. 808-813.
Bialk et al., "Regulation of Gene Editing Activity Directed by Single-Stranded Oligonucleotides and CRISPR/Cas9 Systems," PLoS One 10, e0129308 (2015), pp. 1-19.
Brachman and Kmiec, "Gene repair in mammalian cells is stimulated by the elongation of S phase and transient stalling of replication forks," DNA Repair (Amst). 4, 445-57 (2005).
Brachmann and Kmiec, "DNA replication and transcription direct a DNA strand bias in the process of targeted gene repair in mammalian cells," 2004, Journal of Cell Science, vol. 117, pp. 3867-3874.
Christiana Care Health Systems Press Release, "Modified CRISPR/Cas 9 technique performs more EXACT gene editing. Researchers at the Gene Editing Institute at Christiana Care Health System develop new system to perform precise 'surgery' on the human genome," Jan. 3, 2017.
Drury et al., "DNA pairing is an important step in the process of targeted nucleotide exchange," Nucleic Acids Research, vol. 31, No. 3, pp. 899-910 (2003).
Engstrom and Kmiec, "DNA Replication, cell cycle progression and the targeted gene repair reaction," Cell Cycle vol. 7, No. 10, pp. 1402-1414 (2008).
Engstrom et al., "Regulation of targeted gene repair by intrinsic cellular processes," Bioessays, vol. 31, No. 2, pp. 159-168 (2009).
Ferrara et al., "Recovery of cell cycle delay following targeted gene repair by oligonucleotides," DNA Repair (Amst), vol. 6, No. 10, pp. 1529-1535 (2007).
Ferrara et al., "Targeted gene repair activates Chk1 and Chk2 and stalls replication in corrected cells," DNA Repair (Amst), vol. 5, No. 4, pp. 422-431 (2006).
Hu et al., "Reaction parameters of targeted gene repair in mammalian cells," Mol. Biotechnol, vol. 29, No. 3, pp. 197-210 (2005).
Jinek et a., "A programmable dual-RNA-guided DNA endonuclease in adaptive bacterial immunity," Science, 2012816-821.
Kmiec, "Is the age of genetic surgery finally upon us?" Surg. Oncol., vol. 24, No. 2, pp. 95-99 (2015).
Lin et al., "Enhanced homology-directed human genome engineering by controlled timing of CRISPR/Cas9 delivery," eLife 2013;2:e00471.
Liu et al., "The development and regulation of gene repair," Nat. Rev. Genet., vol. 4, No. 9, pp. 679-689 (2003).
Maruyama et al., "Increasing the efficiency of precise genome editing with CRISPR-Cas9 by inhibition of nonhomologous end joining," Nat. Biotechnol, vol. 33, pp. 538-542 (2015).
Nur-E-Kamal et al., "Single-stranded DNA Induces Ataxia Telangiectasia Mutant (ATM)/p53-dependent DNA Damage and Apoptotic Signals," J. Biol. Chem, vol. 278, No. 14, pp. 12475-12481 (2003).
Olsen et al., "Cellular Responses to Targeted Genomic Sequence Modification Using Single-Stranded Oligonucleotides and Zinc-Finger Nucleases," DNA Repair (Amst), vol. 8, No. 3, pp. 298-308 (2009).
Parekh-Olmedo et al., "Gene therapy progress and prospects: targeted gene repair," (2006) Gene Ther, vol. 12, pp. 639-646.

(Continued)

*Primary Examiner* — Celine X Qian
(74) *Attorney, Agent, or Firm* — McCarter & English, LLP

(57) ABSTRACT

The invention relates to the unexpected discovery of a system and methods for precise homology directed repair after CRISPR/Cas9 cleavage. The invention includes a DNA cleavage and repair system comprising a CRISPR/Cas9 system and an oligonucleotide 100% complementary to cleaved DNA to promote homology directed DNA repair. The invention further includes methods for inducing homology directed repair of cleaved DNA and repairing a CRISPR/Cas9 cleavage.

8 Claims, 19 Drawing Sheets

Specification includes a Sequence Listing.

(56) References Cited

OTHER PUBLICATIONS

Parekh-Olmedo et al., "Progress and Prospects: targeted gene alteration (TGA)," Gene Ther, vol. 14, pp. 1675-1680 (2007).
Radecke et al., "Physical incorporation of a single-stranded oligodeoxynucleotide during targeted repair of a human chromosomal locus.," J. Gene Med, vol. 8, No. 2, pp. 217-228 (2006).
Rivera-Torres et al., "The Position of DNA Cleavage by TALENs and Cell Synchronization Influences the Frequency of Gene Editing Directed by Single-Stranded Oligonucleotides," PLoS One, vol. 9, No. 5, e96483 (2014).
Schumann et al., "Generation of knock-in primary human T cells using Cas9 ribonucleoproteins," Proc. Natl. Acad. Sci. U. S. A., vol. 112, No. 33, p. 10437-10442, 2015.
Strouse et al., "Combinatorial gene editing in mammalian cells using ssODNs and TALENs," Sci. Repm, vol. 4, 3791 (2014).
Voullot et al., "Comparison of T7E1 and Surveyor Mismatch Cleavage Assays to Detect Mutations Triggered by Engineered Nucleases," G3 (Bethesda), vol. 5, pp. 407-415 (2015).
Yu et al., "Progress Towards Gene Therapy for HIV Infection," Gene Therapy, vol. 1, pp. 13-26, 1994.
Yang, Luhan, et al., "Optimization of Scarless Human Stem Cell Genome Editing", Nucleic Acids Research, 2013, vol. 41, No. 19, pp. 9049-9061.
Liu, Mingjie, et al., "Methodologies for Improving HDR Efficiency", Frontiers in Genetics, Jan. 2019, vol. 9, Article 691, pp. 1-9.
Ryu, Seuk-Min, et al., "Evolution of CRISPR Towards Accurate and Efficient Mammal Genome Engineering", BMB Reports, 2019, vol. 51, No. 8, pp. 475-481.

\* cited by examiner

Wild Type eGFP

5-GTGCCCTGGCCCCACCCTGACCACCCTGACCTACGGGCGTGCAGT
3-CACGGGACCGGGGTGGGAGCACTGGACTGGATGCCCGCACGTCA

GCTTCAGCCGCTACCCCGACCACATG-3 (SEQ ID NO: 2)
CGAAGTCGGCGATGGGGCTGGTGTAC-5 (SEQ ID NO: 1)

Mutant eGFP

5-GTGCCCTGGCCCCACCCTGACCACCCTGACCTAGGGGCGTGCAGT
3-CACGGGACCGGGGTGGGAGCACTGGACTGGATCCCCGCACGTCA

GCTTCAGCCGCTACCCCGACCACATG-3 (SEQ ID NO: 3)
CGAAGTCGGCGATGGGGCTGGTGTAC-5 (SEQ ID NO: 17)

72NT

3-C*A*C*GGGACCGGGTGGGAGCACTGGTGGGACTGGATGCCGCACGTCA
CGAAGTCGGCGATGGGGCTGGTG*T*A*C-5 (SEQ ID NO: 1)

Figure 1B

| Cell Cycle Analysis | | | | | |
|---|---|---|---|---|---|
| Treatment | Diploid (%) | Diploid: S-phase (%) | Total S-phase (%) | Debris (%) |
| Unsynchronized | 100 | 41.59 | 41.59 | 17.24 |
| Synchronized No treatment | 90.44 | 32.52 | 29.41 | 11.66 |
| 72-mer ssODN | 98.09 | 29.85 | 29.28 | 12.18 |
| 72-mer ssODN CRISPR-Cas9 | 97.90 | 35.80 | 35.04 | 19.38 |

Figure 4B

Mutant eGFP gene sequence:

5' TCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTT 3' NT (SEQ ID NO:10)

3' AGACGTGGTGGCCGTTCGACGGGCACGGGACCGGGTGGGAGCACTGGTGGGACTGGATGCCGCACGTCACGAAGTCGGCGATGGGGCTGGTGTACTTCGTCGTGCTGAAGAA 5' T (SEQ ID NO:11)

2C

72mer (NT):

3' CTATCTGGACACGGGTGGGACACTGGTGGGACTGGATGCCGCACGTCACGAAGTCGGCGATGGGGCTGGTGTACTTC 5' (SEQ ID NO:1)

Wild Type eGFP gene sequence:

5' TCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTT 3' NT (SEQ ID NO:12)

3' AGACGTGGTGGCCGTTCGACGGGCACGGGACCGGGTGGGAGCACTGGTGGGACTGGATGCCGCACGTCACGAAGTCGGCGATGGGGCTACTTCGTCGTGCTGAAGAA 5' T (SEQ ID NO:13)

| CRISPR | Protospacer (5'-3') | |
|---|---|---|
| 2C | AGCACTGCACGCCCTAGGTC | (SEQ ID NO:14) |

Figure 5

FACS Analyses

COMPOSITIONS AND METHODS FOR IMPROVING HOMOGENEITY OF DNA GENERATED USING A CRISPR/CAS9 CLEAVAGE SYSTEM

CROSS-REFERENCE TO RELATED APPLICATIONS

The present application claims priority under 35 U.S.C. § 119(e) to U.S. Provisional Patent Application No. 62/277,212, filed Jan. 11, 2016, and U.S. Provisional Patent Application No. 62/442,145, filed Jan. 4, 2017, all of which are incorporated herein by reference in their entireties.

STATEMENT REGARDING FEDERALLY SPONSORED RESEARCH OR DEVELOPMENT

This invention was made with government support under GM109021-02 awarded by National Institutes of Health. The government has certain rights in the invention.

BACKGROUND OF THE INVENTION

Knocking genes out (also known as "gene knockouts" or "gene knock-outs") using the CRISPR/Cas9 system has proven much easier than knocking genes in (also known as "gene knockins" or "gene knock-ins") using that system, because double-stranded breaks induced by the Cas9 nuclease are more quickly repaired by the non-homologous end-joining (NHEJ) DNA repair mechanism. It should be noted that NHEJ often drops nucleotides from the ends being joined. This works well for inducing gene knock-outs (because it leads to a frameshift), but is not ideal for gene knock-ins (which requires greater precision).

There is thus a need to promote precise gene editing using the CRISPR/Cas9 systems. Unfortunately, the homology-directed repair (HDR) pathway, which allows for insertion of precise genetic modifications, has low efficiency compared with the NHEJ pathway. Eliminating Ku heterodimer proteins and DNA ligase IV involved in the NHEJ pathway increases efficiency of HDR. However, the most effective way of inhibiting the error-prone NHEJ pathway is to degrade these molecules with adenovirus 4 proteins. This approach relies on specific or targeted degradation of native DNA repair machinery, and does not provide an optimal approach for gene therapy.

Therefore, a need exists in the art for efficient and precise gene editing methods, which can be used for example in gene therapy. Such methods should allow gene knock-ins using CRISPR/Cas9 technologies without frameshift. The present invention satisfies this need.

BRIEF SUMMARY OF THE INVENTION

As described herein, the present invention relates in part to compositions and methods for promoting precise gene editing (such as, but not limited to, "knock-in" and/or "knock-out") using CRISPR/Cas9 systems.

In one aspect, the invention includes a method for promoting DNA cleavage and repair in a cell. In another aspect, the invention includes a method for inducing homology directed repair of a DNA cleaved by a CRISPR/Cas9 system in a cell.

In certain embodiments, the method utilizes at least one CRISPR/Cas9 system and a deoxyoligonucleotide. The at least one CRISPR/Cas9 system cleaves in a cell a DNA in one or more sites, and generates a first cleavage end and a second cleavage end on the DNA. The deoxyoligonucleotide comprises two regions, wherein the first region is complementary to the first generated cleavage end and at least one deoxynucleotide adjacent to the first generated cleavage end of the DNA, and wherein the second region is complementary to the second generated cleavage end and at least one deoxynucleotide adjacent to the second generated cleavage end of the DNA. In certain embodiments, the first region of the deoxyoligonucleotide anneals to the first generated cleavage end and the at least one deoxynucleotide adjacent to the first cleavage end of the DNA, and the second region of the deoxyoligonucleotide anneals to the second generated cleavage end and the at least one deoxynucleotide adjacent to the second cleavage end of the DNA. In certain embodiments, the DNA is cleaved and repaired with no insertion or deletion of one or more unwanted deoxynucleotides at the junction of the first and second cleavage ends of the DNA.

In yet another aspect, the invention includes a method of promoting fusion, without insertion or deletion of unwanted deoxynucleotides, of first and second cleavage ends of a DNA that was cleaved by a CRISPR/Cas9 system in a cell. The method comprises providing a DNA that has been cleaved in one or more sites by at least one CRISPR/Cas9 system in the cell, wherein the cleaved DNA comprises a first cleavage end and a second cleavage end. The method further comprises annealing to the cleaved DNA a deoxyoligonucleotide comprising two regions, wherein the first region is complementary to the first generated cleavage end and at least one deoxynucleotide adjacent to the first generated cleavage end of the DNA, and wherein the second region is complementary to the second generated cleavage end and at least one deoxynucleotide adjacent to the second generated cleavage end of the DNA. In certain embodiments, homology directed repair is induced at the generated cleavage ends with no insertion or deletion of one or more unwanted deoxynucleotides at the junction of the first and second cleavage ends.

In one aspect, the invention includes a method for promoting DNA fusing and repair in a cell. In another aspect, the invention includes a method for inducing homology directed fusing of a first DNA cleaved by a CRISPR/Cas9 system in a cell with a second DNA.

In certain embodiments, the method utilizes at least one CRISPR/Cas9 system and a deoxyoligonucleotide. The at least one CRISPR/Cas9 system cleaves in a cell a first DNA in one or more sites, and generates a first cleavage end on the DNA. A second DNA, which is to be fused to the first DNA, comprises at least a second cleavage end. The deoxyoligonucleotide comprises two regions, wherein the first region is complementary to the first generated cleavage end and at least one deoxynucleotide adjacent to the first generated cleavage end of the first DNA, and wherein the second region is complementary to the second cleavage end and at least one deoxynucleotide adjacent to the second cleavage end of the second DNA. In certain embodiments, the first region of the deoxyoligonucleotide anneals to the first generated cleavage end and the at least one deoxynucleotide adjacent to the first cleavage end of the first DNA, and the second region of the deoxyoligonucleotide anneals to the second cleavage end and the at least one deoxynucleotide adjacent to the second cleavage end of the second DNA. In other embodiments, the first DNA is fused to the second DNA with no insertion or deletion of one or more unwanted deoxynucleotides at the junction of the first cleavage end of the first DNA and the second cleavage end of the second DNA.

In yet another aspect, the invention includes a method of promoting fusion, without insertion or deletion of unwanted deoxynucleotides, of a first cleavage end of a first DNA that was cleaved by a CRISPR/Cas9 system in a cell with a second cleavage end of a second DNA. The method comprises providing a first DNA that has been cleaved at a first cleavage site by at least one CRISPR/Cas9 system in the cell, and a second DNA comprising a second cleavage site. The method further comprises annealing to the first and second DNAs a deoxyoligonucleotide comprising two regions, wherein the first region is complementary to the first generated cleavage end and at least one deoxynucleotide adjacent to the first generated cleavage end of the first DNA, and wherein the second region is complementary to the second cleavage end and at least one deoxynucleotide adjacent to the second cleavage end of the second DNA. In certain embodiments, fusing with homology directed repair of the first and second DNAs is promoted, with no insertion or deletion of one or more unwanted deoxynucleotides at the junction of the first cleavage end of the first DNA and the second cleavage end of the second DNA.

In yet another aspect, the invention provides a kit for promoting DNA cleavage and repair in a cell. In yet another aspect, the invention provides a kit for inducing homology directed repair of a DNA cleaved by a CRISPR/Cas9 system in a cell.

In certain embodiments, the kit comprises at least one CRISPR/Cas9 system, which cleaves in a cell a DNA in one or more sites, and generates a first cleavage end and a second cleavage end on the DNA. In other embodiments, the kit further comprises a deoxyoligonucleotide comprising two regions, wherein the first region is complementary to the first generated cleavage end and at least one deoxynucleotide adjacent to the first generated cleavage end of the DNA, and wherein the second region is complementary to the second generated cleavage end and at least one deoxynucleotide adjacent to the second generated cleavage end of the DNA.

In yet another aspect, the invention provides a kit for promoting DNA fusing and repair in a cell. In yet another aspect, the invention provides a kit for inducing homology directed fusing of a first DNA cleaved by a CRISPR/Cas9 system in a cell with a second DNA.

In certain embodiments, the kit comprises at least one CRISPR/Cas9 system, which cleaves in a cell a DNA in one or more sites, and generates a first cleavage end on the DNA. In other embodiments, the kit further comprises a second DNA comprising a second cleavage end. In yet other embodiments, the kit further comprises a deoxyoligonucleotide comprising two regions, wherein the first region is complementary to the first generated cleavage end and at least one deoxynucleotide adjacent to the first generated cleavage end of the first DNA, and wherein the second region is complementary to the second cleavage end and at least one deoxynucleotide adjacent to the second cleavage end of the second DNA.

In various embodiments of the above aspects or any other aspect of the invention delineated herein, the deoxyoligonucleotide comprises about 25 to about 200 deoxynucleotides in length. In other embodiments, the one or more unwanted insertion or deletion comprises a single deoxynucleotide. In yet other embodiments, the one or more unwanted insertion or deletion comprises more than one deoxynucleotide. In yet other embodiments, the at least one deoxynucleotide adjacent to the first generated cleavage end comprises about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98 and/or 100 deoxynucleotides. In yet other embodiments, the at least one deoxynucleotide adjacent to the second generated cleavage end comprises about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98 and/or 100 deoxynucleotides. In yet other embodiments, the first region is directly linked to the second region. In yet other embodiments, the first region is linked to the second region through an oligonucleotide comprising about 1, 2, 4, 6, 8, 10, 12, 14, 16, 18, 20, or any fraction or multiple thereof, deoxynucleotides. In yet other embodiments, the CRISPR/Cas9 system is derived from a plasmid.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1B illustrates the sequence of a ssODN used in a gene editing system (SEQ ID NO: 1) aligned with the wild-type (SEQ ID NO: 2) and mutant eGFP gene (SEQ ID NO: 3). The wild-type and mutated eGFP gene segments with the target codon located in the center of the sequences are shown. The nucleotide targeted for exchange is emphasized in bold and underlined. Phosphorothioate modified and end protected (denoted with *) 72NT, a 72-mer, used to target the non-transcribed (NT) strand of the mutated eGFP gene is shown.

FIG. 4B is a table illustrating percentages of cells present in the cell cycle stages measured in FIG. 4A.

FIG. 5 illustrates a model system for gene editing of the mutant eGFP gene. The appropriate segments of the wild-type and mutated eGFP gene with the targeted codon, located in the center of the sequence, are displayed. The nucleotide targeted for exchange is bolded and underlined. The oligonucleotide used in these experiments is 72 bases in length bearing phosphorothioate modified linkages at the three terminal bases; the 72-mer targets the non-transcribed (NT) strand (72NT).

DETAILED DESCRIPTION OF THE INVENTION

Definitions

Figure 1A:
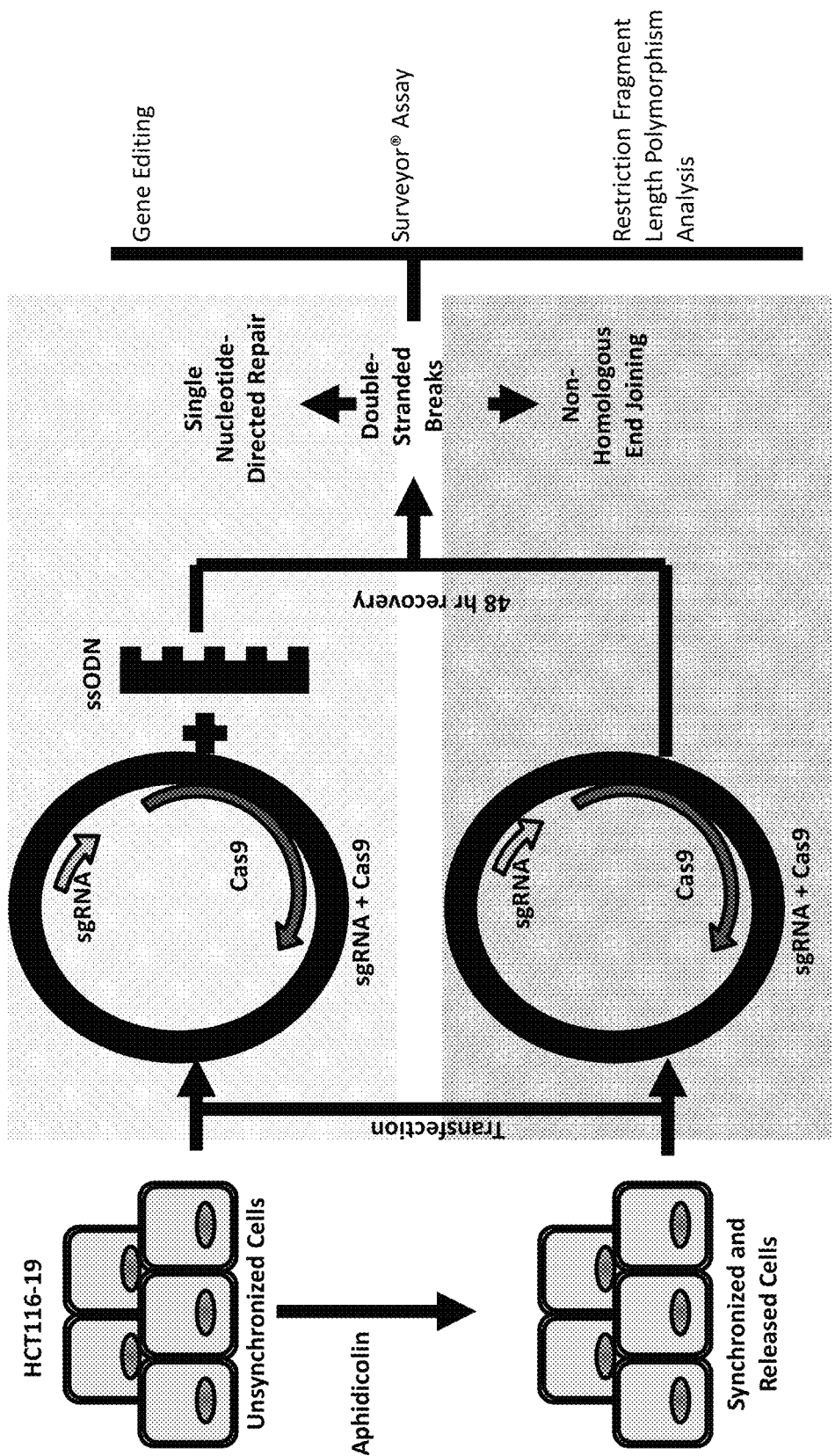
FIG. 1A is a schematic diagram illustrating an experimental workflow of certain methods described herein. HCT116-19 cells are either unsynchronized or synchronized and released, then transfected with a CRISPR/Cas9 expression vector (pX330) with or without a single stranded oligodeoxynucleotide (ssODN). After 48 hours, the cells are analyzed for gene editing activity, Surveyor endonuclease digestion, and RFLP.

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, specific materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more specifically ±5%, even more specifically ±1%, and still more specifically ±0.1% from the specified value, as such variations are appropriate to perform the disclosed methods.

As used herein the term "amount" refers to the abundance or quantity of a constituent in a mixture.

As used herein, the term "amplicon" or "PCR products" or "PCR fragments" or "amplification" products refers to extension products that comprise the primer and the newly synthesized copies of the target sequences.

As used herein, the term "bp" refers to base pair.

The term "complementary" refers to the degree of anti-parallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore various DNA repair functions as well as regulatory functions are based on base pair complementarity.

The term "concentration" refers to the abundance of a constituent divided by the total volume of a mixture. The term concentration can be applied to any kind of chemical mixture, but most frequently it refers to solutes and solvents in solutions.

The term "CRISPR/Cas" or "clustered regularly interspaced short palindromic repeats system" or "CRISPR" interchangeably refers to DNA loci containing short repetitions of base sequences. Each repetition is followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage. To direct Cas9 to cleave sequences of interest, crRNA-tracrRNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics. In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of invading DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter "Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "measuring" according to the present invention relates to determining the amount or concentration, preferably semi-quantitatively or quantitatively. Measuring can be done directly and/or indirectly.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "mutation" as used therein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, one skilled in the art "obtains" an experimental result, data set, material, conclusion or any other piece of knowledge when one comes into possession of such experimental result, data set, material, conclusion or any other piece of knowledge, which may have been acquired by one or more third parties or by the one skilled in the art in its entirety or at least partially. In certain embodiments, one skilled in the art obtains experimental data, which may be raw data or at least partially processed data, and processes and/or manipulates the data as to reach at least one scientific conclusion or inference. In other embodiments, one skilled in the art obtains at least one scientific conclusion or inference that is derived from experimental data by one or more third parties' processing and/or manipulation. In other embodiments, one skilled in the art obtains at least one material that is identified and/or prepared by one or more third parties.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" includes cDNA, RNA, DNA/RNA hybrid, anti-sense RNA, siRNA, miRNA, snoRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

A "primer" is an oligonucleotide, usually of about 15, 20, 25, 30, 35, 40, 45 or 50 nucleotides in length, that is capable of hybridizing in a sequence specific fashion to the target sequence and being extended during the PCR.

The term "promoter" as used herein is defined as a DNA sequence recognized by the synthetic machinery of the cell, or introduced synthetic machinery, required to initiate the specific transcription of a polynucleotide sequence.

As used herein, the terms "reference" or "control" are used interchangeably, and refer to a value that is used as a standard of comparison.

The term "RNA" as used herein is defined as ribonucleic acid.

A "sample" or "biological sample" as used herein means a biological material from a subject, including but is not limited to organ, tissue, exosome, blood, plasma, saliva, urine and other body fluid. A sample can be any source of material obtained from a subject.

A "single nucleotide polymorphism" (SNP), as referred herein, represents a variation in one or more single nucleotide changes in a DNA sequence among organisms, such among viruses, among mammals, or among humans. For instance, a SNP may replace the nucleotide cytosine (C) with the nucleotide thymine (T) in a certain stretch of DNA. SNPs are the most common type of genetic variation among people and occur normally throughout a person's DNA (around 10 million SNPs in the human genome). Most commonly, these variations are found in the non-coding DNA between genes. They can act as biological markers and can be associated with certain diseases particularly when they occur within a gene or in a regulatory region near a gene. In the cases where SNPs occur within a gene, they may lead to variations in the amino acid sequence. SNPs can help predicting an individual's response to certain drugs, susceptibility to environmental factors such as toxins, and risk of developing particular diseases.

A "subject" or "patient" as used therein may be a human or non-human mammal. Non-human mammals include, for example, livestock and pets, such as ovine, bovine, porcine, canine, feline and murine mammals. In certain embodiments, the subject is human.

The term "therapeutic" as used herein means a treatment and/or prophylaxis. A therapeutic effect is obtained by suppression, remission, or eradication of a disease state.

As used herein, to "treat" means reducing the frequency with which symptoms of a disease, disorder, or adverse condition, and the like, are experienced by a subject.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

A "vector" is a composition of matter comprising an isolated nucleic acid, and can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention relates in one aspect to the unexpected discovery of a system and methods for precise homology directed repair (HDR) after CRISPR/Cas9 cleavage. The invention includes a DNA cleavage and repair method comprising a CRISPR/Cas9 system that cleaves DNA generating cleavage ends, and an oligonucleotide that is complementary to each of the generated cleavage ends and nucleotides adjacent to the cleavage ends. In certain embodiments, the oligonucleotide is capable of annealing to the generated cleavage ends and adjacent nucleotides with no unwanted insertion or deletion to the cleaved DNA. The invention further includes methods for inducing homology directed repair of cleaved DNA and repairing a CRISPR/Cas9 cleavage.

CRISPR/Cas

The CRISPR/Cas system is a facile and efficient system for inducing targeted genetic alterations. Target recognition by the Cas9 protein requires a 'seed' sequence within the guide RNA (gRNA) and a conserved tri-nucleotide containing protospacer adjacent motif (PAM) sequence upstream of the gRNA-binding region. The CRISPR/CAS system can thereby be engineered to cleave virtually any DNA sequence by redesigning the gRNA for use in cell lines (such as 293T cells), primary cells, and CAR T cells. The CRISPR/CAS system can simultaneously target multiple genomic loci by co-expressing a single Cas9 protein with two or more gRNAs, making this system uniquely suited for multiple gene editing or synergistic activation of target genes.

One example of a CRISPR/Cas system used to inhibit gene expression, CRISPRi, is described in U.S. Publication No. US2014/0068797, which is incorporated herein by reference in its entirety. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR system comprises an expression vector, such as, but not limited to, an pAd5F35-CRISPR vector. In other embodiments, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

The guide nucleic acid sequence is specific for a gene and targets that gene for Cas endonuclease-induced double strand breaks. The sequence of the guide nucleic acid sequence may be within a loci of the gene. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for any gene, such as a gene that would reduce immunogenicity or reduce sensitivity to an immunosuppressive microenvironment. The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional. In certain embodiments, the tracr sequence has at least 50%, 60%, 70%, 80%, 90%, 95% or 99% of sequence complementarity along the length of the tracr mate sequence when optimally aligned. In other embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in US20110059502, incorporated herein by reference. In certain embodiments, a tagged CRISPR enzyme is used to identify the location of a target sequence.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Another delivery mode for the CRISPR/Cas9 comprises a combination of RNA and purified Cas9 protein in the form of a Cas9-guide RNA ribonucleoprotein (RNP) complex. (Lin et al., 2014, ELife 3:e04766). Viral vector delivery systems include DNA and RNA viruses, which have either episomal or integrated genomes after delivery to the cell (Anderson, 1992, Science 256:808-813; and Yu et al., 1994, Gene Therapy 1:13-26).

In certain embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus*, or other species. In certain embodiments, Cas9 can include: spCas9, Cpf1, CasY, CasX, or saCas9.

In general, CRISPR/Cas proteins comprise at least one RNA recognition and/or RNA binding domain. RNA recognition and/or RNA binding domains interact with the guiding RNA. CRISPR/Cas proteins can also comprise nuclease domains (i.e., DNase or RNase domains), DNA binding domains, helicase domains, RNAse domains, protein-protein interaction domains, dimerization domains, as well as other domains. The CRISPR/Cas proteins can be modified to increase nucleic acid binding affinity and/or specificity, alter an enzymatic activity, and/or change another property of the protein. In certain embodiments, the CRISPR/Cas-like protein of the fusion protein can be derived from a wild type Cas9 protein or fragment thereof. In other embodiments, the CRISPR/Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. ($4^{th}$ Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Homology Directed Repair

In one aspect, the invention includes a DNA cleavage and repair system. The system comprises a CRISPR/Cas9 system, wherein the system creates cleavage ends in a DNA, and an oligonucleotide 100% complementary to each of the cleavage ends and nucleotides adjacent to the cleavage ends, wherein the oligonucleotide is capable of annealing or hybridizing to the cleavage ends and adjacent nucleotides with no insertion or deletion. In certain embodiments, the oligonucleotide contains a single mismatch to the cleavage ends and nucleotides adjacent to the cleavage ends, wherein the oligonucleotide is capable of annealing or hybridizing to the cleavage ends and adjacent nucleotides with no insertion or deletion. The oligonucleotide can be about 40 to about 200 nucleotides (nts) in length and complementary to the DNA. The oligonucleotide is capable of annealing or hybridizing to the DNA recognized by the CRISPR/Cas9 system. The oligonucleotides include complementary sequences to the CRISPR/Cas9 cleaved DNA. The oligonucleotides may be engineered to be between about 40 nucleotides to about 200 nucleotides, or about 50 nucleotides to about 125 nucleotides, or about 60 nucleotides to about 100 nucleotides, or about 70 nucleotides to about 90 nucleotides in length. The oligonucleotide can be about 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 160, 170, 180, 190, 200 nucleotides, or any number of nucleotides therebetween. In one embodiment, the oligonucleotide is greater than 60 nucleotides in length. In another embodiment, the oligonucleotide is greater than 70 nucleotides in length. In yet another embodiment, the oligonucleotide is about 72 nucleotides in length.

Methods

In one aspect, the invention includes a method for promoting DNA cleavage and repair in a cell. In another aspect, the invention includes a method for inducing homology directed repair of a DNA cleaved by a CRISPR/Cas9 system in a cell.

In certain embodiments, the method utilizes at least one CRISPR/Cas9 system and a deoxyoligonucleotide. The at least one CRISPR/Cas9 system cleaves in a cell a DNA in one or more sites, and generates a first cleavage end and a second cleavage end on the DNA. The deoxyoligonucleotide comprises two regions, wherein the first region is complementary to the first generated cleavage end and at least one deoxynucleotide adjacent to the first generated cleavage end of the DNA, and wherein the second region is complementary to the second generated cleavage end and at least one deoxynucleotide adjacent to the second generated cleavage end of the DNA. In certain embodiments, the first region of the deoxyoligonucleotide anneals to the first generated cleavage end and the at least one deoxynucleotide adjacent to the first cleavage end of the DNA, and the second region of the deoxyoligonucleotide anneals to the second generated cleavage end and the at least one deoxynucleotide adjacent to the second cleavage end of the DNA. In certain embodiments, the DNA is cleaved and repaired with no insertion or deletion of one or more unwanted deoxynucleotides at the junction of the first and second cleavage ends of the DNA.

In yet another aspect, the invention includes a method of promoting fusion, without insertion or deletion of unwanted deoxynucleotides, of first and second cleavage ends of a DNA that was cleaved by a CRISPR/Cas9 system in a cell. The method comprises providing a DNA that has been cleaved in one or more sites by at least one CRISPR/Cas9 system in the cell, wherein the cleaved DNA comprises a first cleavage end and a second cleavage end. The method further comprises annealing to the cleaved DNA a deoxyoligonucleotide comprising two regions, wherein the first region is complementary to the first generated cleavage end and at least one deoxynucleotide adjacent to the first generated cleavage end of the DNA, and wherein the second region is complementary to the second generated cleavage end and at least one deoxynucleotide adjacent to the second generated cleavage end of the DNA. In certain embodiments, homology directed repair is induced at the generated cleavage ends with no insertion or deletion of one or more unwanted deoxynucleotides at the junction of the first and second cleavage ends.

In one aspect, the invention includes a method for promoting DNA fusing and repair in a cell. In another aspect, the invention includes a method for inducing homology directed fusing of a first DNA cleaved by a CRISPR/Cas9 system in a cell with a second DNA.

In certain embodiments, the method utilizes at least one CRISPR/Cas9 system and a deoxyoligonucleotide. The at least one CRISPR/Cas9 system cleaves in a cell a first DNA in one or more sites, and generates a first cleavage end on the DNA. A second DNA, which is to be fused to the first DNA, comprises at least a second cleavage end. The deoxyoligonucleotide comprises two regions, wherein the first region is complementary to the first generated cleavage end and at least one deoxynucleotide adjacent to the first generated cleavage end of the first DNA, and wherein the second region is complementary to the second cleavage end and at least one deoxynucleotide adjacent to the second cleavage end of the second DNA. In certain embodiments, the first region of the deoxyoligonucleotide anneals to the first generated cleavage end and the at least one deoxynucleotide adjacent to the first cleavage end of the first DNA, and the second region of the deoxyoligonucleotide anneals to the second cleavage end and the at least one deoxynucleotide adjacent to the second cleavage end of the second DNA. In other embodiments, the first DNA is fused to the second DNA with no insertion or deletion of one or more unwanted deoxynucleotides at the junction of the first cleavage end of the first DNA and the second cleavage end of the second DNA.

In yet another aspect, the invention includes a method of promoting fusion, without insertion or deletion of unwanted deoxynucleotides, of a first cleavage end of a first DNA that was cleaved by a CRISPR/Cas9 system in a cell with a second cleavage end of a second DNA. The method comprises providing a first DNA that has been cleaved at a first cleavage site by at least one CRISPR/Cas9 system in the cell, and a second DNA comprising a second cleavage site. The method further comprises annealing to the first and second DNAs a deoxyoligonucleotide comprising two regions, wherein the first region is complementary to the first generated cleavage end and at least one deoxynucleotide adjacent to the first generated cleavage end of the first DNA, and wherein the second region is complementary to the second cleavage end and at least one deoxynucleotide adjacent to the second cleavage end of the second DNA. In certain embodiments, fusing with homology directed repair of the first and second DNAs is promoted, with no insertion or deletion of one or more unwanted deoxynucleotides at the junction of the first cleavage end of the first DNA and the second cleavage end of the second DNA.

By "unwanted insertions or deletions" is meant (insertions or deletions) that would disrupt the cleavage site or the area surrounding the cleavage site by adding or deleting nucleotide bases. The sizes of the unwanted insertions or deletions can be a single nucleotide base or many nucleotide bases. For example, in a typical CRISPR/Cas9 cleavage, 4 nucleotide bases may be deleted, causing a frameshift in the nucleotide sequence (an unwanted deletion). The present invention provides methods for avoiding unwanted insertions or deletions following CRISPR/Cas9 cleavage activity. In certain embodiments, the methods of the present invention can include inserting or deleting (wanted) nucleotides/genes of interest. For example, following CRISPR/Cas9 cleavage, a gene of interest can to be inserted into a piece of DNA at the cleavage site without any insertions or deletions of additional (unwanted) nucleotides.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Improving Homogeneity of DNA Generated Using a CRISPR/Cas9 Cleavage System The materials and methods employed in these experiments are now described.

CRISPR/Cas9. Synchronized HCT116-19 cells were electroporated with an increasing dose of a plasmid containing a CRISPR/Cas9 expression construct targeting the mutant eGFP gene, as well as an increasing dose of the same construct with a 72 mer ssODN complementary to the eGFP gene with a single mismatch at the mutant eGFP base. Forty-eight hours after electroporation, the samples were analyzed via FACS, restriction fragment length polymorphism analysis (RFLP), and SURVEYOR MUTATION DETECTION® kits (Integrated DNA Technologies).

Restriction fragment length polymorphism analysis. An AvrII restriction site located around the mutant base of the eGFP gene served as a read out of Cas9 induced DNA damage. When Cas9 cleaves the target site and gets repaired via non-homologous end joining, base pairs can be lost, resulting in destruction of the AvrII restriction site. After digestion and gel separation of a population of cells that were transfected with the eGFP targeting CRISPR/Cas9, the CRISPR/Cas9 activity was calculated as the percentage of the DNA which was resistant to AvrII digestion due to the loss of the restriction site.

An alternative assay to RFLP analysis for the establishment of CRISPR/Cas9 activity at the target site is the SURVEYOR MUTATION DETECTION® kit (Integrated DNA Technologies), which utilizes a unique endonuclease formulation that cleaves with high specificity at a mismatch in a DNA strand. PCR amplicons of the target site in the population of cells treated with the CRISPR/Cas9 construct were denatured and rehybridized, resulting in duplex formations from a mix of amplicons, some containing a mismatch due to a Cas9 induced altered sequence strand hybridizing with an unaltered sequence strand. This pool of duplexes was then digested with the endonuclease and the products were separated on a polyacrylamide gel, followed by densitometry to calculate intensities of the digested and undigested products. Indel occurrence was calculated using a set of formulas based on the binomial probability distribution of duplex formation:

fraction cleaved=(digested products)/(digested products+undigested product) indel (%)=100(1−√(1−fraction cleaved))

Measuring gene editing. When the mutant base in the eGFP gene is corrected in a cell transfected with the CRISPR/Cas9 construct and the 72 mer ssODN, eGFP fluorescence is restored and the cell glows green. FACS analysis of gene editing efficiency was performed on a population of cells which were transfected with the CRISPR/Cas9 construct and the ssODN. The efficiency was calculated as the percentage of the cell population in which eGFP fluorescence was restored.

Cell Line and Culture Conditions. HCT116 cells were acquired from ATCC (American Type Cell Culture, Manassas, Va.). The HCT116-19 was created by integrating a pEGFP-N3 vector (Clontech, Palo Alto, Calif.) containing a mutated eGFP gene (Hu et al., 2005, Molecular Biotechnology 29:197-210). The mutated eGFP gene has a nonsense mutation at position +67 resulting in a nonfunctional eGFP protein (Brachman et al., 2004, J. Cell Sci. 117:3867-74). HCT116-19 cells were cultured in McCoy's 5A Modified medium (Thermo Scientific, Pittsburgh, Pa.) supplemented with 10% fetal bovine serum, 2 mM L-Glutamine, and 1% Penicillin/Streptomycin. Cells were maintained at 37° C. and 5% $CO_2$. The custom designed 72 mer oligonucleotide was synthesized by IDT (Integrated DNA Technologies, Coralville, Iowa).

CRISPR Design and Construction. The guide RNA and CRISPR/Cas9 system used for gene editing in this system was described in Bialk et al., 2015, PLoS One 10:e0129308), which is incorporated herein in its entirety. CRISPR/Cas9 was constructed using standard cloning methods following the latest oligo annealing and backbone cloning protocol with single-step digestion-ligation. The gRNA was cloned into pX330 backbone vector (Addgene plasmid 42230), a human codon-optimized SpCas9 and chimeric guide RNA expression plasmid. pX330 was purchased through Addgene (www dot addgene dot org). Following construction, clones were verified by DNA sequencing by Genewiz Incorporated (South Plainfield, N.J.).

Transfection of HCT116-19 Cells and Experimental Approach. For experiments utilizing synchronized cells, HCT116-19 cells were seeded at $2.5 \times 10^6$ cells in a 100 mm dish and synchronized with 6 µM aphidicolin for 24 hours prior to targeting. Cells were released for 4 hours prior to trypsinization and transfection by washing with PBS (−/−) and adding complete growth media. Synchronized and unsynchronized HCT116-19 cells were simultaneously transfected at a concentration of $5 \times 10^5$ cells/100 µl in 4 mm gap cuvette (BioExpress, Kaysville, Utah). Single-stranded oligonucleotides and pX330 constructs were electroporated (250V, LV, 13 ms pulse length, 2 pulses, is interval) using a Bio-Rad Gene Pulser XCell™ Electroporation System (Bio-Rad Laboratories, Hercules, Calif.). Cells were then recovered in 6-well plates with complete growth media at 37° C. for 24-48 hours prior to analysis.

Analysis of Gene Edited Cells. Fluorescence (eGFP⁺) was measured by a Guava EasyCyte 5HT Flow Cytometer (Millipore, Temecula, Calif.). Cells were harvested by trypsinization, washed once with 1×PBS (−/−) and resuspended in buffer (0.5% BSA, 2 mM EDTA, 2 µg/mL Propidium Iodide (PI) in PBS−/−). Propidium iodide was used to measure cell viability as such, viable cells stain negative for PI (uptake). Correction efficiency was calculated as the percentage of the total live eGFP positive cells over the total live cells in each sample.

RFLP Analysis of CRISPR/Cas9 Cleavage Activity. HCT116-19 cells were electroporated at a concentration of $5 \times 10^5$ cells/100 µl in 4 mm gap cuvette (BioExpress, Kaysville, Utah) with pX330 or pX330 and 1.35 µg of the 72 mer ssODN. Cells were then recovered in 6-well plates with complete growth media at 37° C. for 72 hours. DNA was isolated using the Blood and Tissue DNeasy kit (Qiagen, Hilden, Germany). RFLP analysis was performed on 605 bp amplicons that were created using forward primer, 5'CTGGACGGCGACGTAAACGGC (SEQ ID NO: 4) and reverse primer, 5'ACCATGTGATCGCGCTTCTCG (SEQ ID NO: 5). PCR samples were purified using the QIAquick PCR purification kit (Qiagen, Hilden, Germany) and treated with the AvrII restriction enzyme following the manufactures protocol. Digested samples were loaded along with NEB 2-log DNA ladder (NEB, Ipswich, Mass.) into a 5-20% TBE acrylamide gel for analysis. SYBR Gold (Invitrogen, Carlsbad, Calif.) was used to stain the gel and images were acquired by the Gel Doc EZ System (BioRad, Hercules, Calif.) to create an electrophoregram. Using Bio Rad's Image Lab software, automated lane detection was performed, followed by selecting bands. Using the software, the concentration of each band represented by a peak on the electrophoregram was derived from the area of each peak as a percent of the total lane peak area.

SURVEYOR Analysis of CRISPR/Cas9 Cleavage Activity. HCT116-19 cells were electroporated at a concentration of $5 \times 10^5$ cells/100 μl in 4 mm gap cuvette (BioExpress, Kaysville, Utah) with pX330 or pX330 and 1.35 μg of the 72 mer ssODN. Cells were then recovered in 6-well plates with complete growth media at 37° C. for 72 hours. DNA was isolated using the Blood and Tissue DNeasy kit (Qiagen, Hilden, Germany). The Surveyor assay was performed on 605 bp amplicons that were created using forward primer, 5'CTGGACGGCGACGTAAACGGC (SEQ ID NO: 4) and reverse primer, 5'ACCATGTGATCGCGCTTCTCG (SEQ ID NO: 5). PCR samples were purified using the QIAquick PCR purification kit (Qiagen, Hilden, Germany). 200 ng of each PCR product was mixed with 200 ng of PCR product from the untreated sample and subjected to a heteroduplex formation: 95° C. for 10 minutes, 95° C. to 85° C. with a ramp rate of −2° C./s, 85° C. for 1 minute to 75° C. at −0.1° C./s, 75° C. for 1 minute to 65° C. at −0.1° C./s, 65° C. for 1 minute to 55° C. at −0.1° C./s, 55° C. for 1 minute to 45° C. at −0.1° C./s, 45° C. for 1 minute to 35° C. to 25° C. at −0.1° C./s, 25° C. for 1 minute. After duplex formation products were treated with SURVEYOR Nuclease S and SURVEYOR Enhancer S (IDT Technologies) for 30 minutes at 42° C., gel electrophoresed and stained with SYBR Safe DNA stain (Life Technologies). Gels were imaged with a Gel Doc EZ Imager (Bio-Rad) and densitometry was performed by measuring the area under the curves of each band, using the Image Lab software (Bio-Rad). Calculations were based on the following formulas:

% cleaved=sum of cleaved products/sum of cleavage products+parent band.

Cell Cycle Analysis. For experiments utilizing synchronized cells, HCT116-19 cells were seeded at $2.5 \times 10^6$ cells in a 100 mm dish and synchronized with 6 μM aphidicolin for 24 hours. Cells were released for 4 hours prior to trypsinization and transfection by washing with PBS (−/−) and adding complete growth media. Synchronized and unsynchronized HCT116-19 cells were simultaneously transfected at a concentration of $5 \times 10^5$ cells/100 μl in 4 mm gap cuvette (BioExpress, Kaysville, Utah). Single-stranded oligonucleotide and/or CRISPR plasmid constructs were electroporated at the indicated concentration (250V, LV, 13 ms pulse length, 2 pulses, 1s interval) using a Bio-Rad Gene Pulser XCell Electroporation System (Bio-Rad Laboratories, Hercules, Calif.). Cells were then recovered in 6-well plates with complete growth media at 37° C. for 24 hours.

For cell cycle analysis, cells were harvested and washed in PBS. They were then spun at 450 g for 5 minutes, re-suspended in 500 μl cold PBS and fixed by adding 5 ml of 70% cold ethanol while vortexing followed by an overnight incubation at 4° C. After fixation, the cells were centrifuged for 5 minutes at 450 g, washed once with PBS and then re-suspended in 200 μl of PBS and 200 μl of pre-warmed Guava® Cell Cycle Reagent. The cells were incubated away from light at 37° C. for 30 min followed by analysis through flow cytometry. DNA content was analyzed by a Guava EasyCyte 5HT Flow Cytometer (Millipore, Temecula, Calif.) using the Guava EasyCyte Cell Cycle Software Module. Cell cycle modeling was performed and the percent of cells in G0-G1, S and G2-M phase was calculated using Modfit (Verity Software House, Topsham, Me.).

Cell cycle modeling was performed using the auto analysis feature of the Modfit software. S-phase events were monitored to determine if there would be an extension of S-phase induced by the presence of CRISPR/Cas9 at increasing concentrations of plasmid. The main focus of the analysis was given to the three specific parameters associated with S-phase: diploid (%), percent of all events that are associated with a single cycling population; diploid: S-phase (%), percent of all cells in the diploid cycle; and Total S-Phase (%) (Average S-Phase), the sum of all S-Phase areas as a percentage of the total area for cycling cells of all populations. Debris (%) was also analyzed to determine the quality of the analyzed data.

Results of the experiments are now described.

Single-stranded oligonucleotides can be used to direct the repair of a mutant base in mammalian chromosomes in a precise fashion. The method, by which single agent gene editing takes place has been elucidated with the mechanism of action and the regulatory circuitry that surrounds it well defined. A number of important reaction parameters that control the frequency include having the targeted cells progressing through S phase and undergoing active DNA replication. In addition, the introduction of a double strand DNA break at or near the target site elevates the population of targeted cells exhibiting the desired genotype and phenotype. Using this knowledge base as a backdrop, combinatorial gene editing with single-stranded oligonucleotides and a CRISPR/Cas9 system was used to execute single nucleotide exchange.

The repair of a single point mutation by gene editing can be evaluated using the well-established reporter gene system, which consists of a single copy of a mutant eGFP gene integrated into HCT116 cells (Hu et al., 2005, Mol. Biotechnol. 29:197-210, Engstrom et al., 2009, Bioessays 31:159-68, Mali et al., 2003, *Nat. Rev. Genet.* 4:679-89). Repair of this mutation is executed by the combined action of a specifically designed single-stranded oligonucleotide, 72 bases in length, and a CRISPR/Cas9 system (Bialk et al., 2015, PLoS One 10:e0129308). The cells can be targeted in either an unsynchronized or synchronized (at the G1/S border by aphidicolin) state followed by release (FIG. 1A). Synchronization and release optimizes the percentage of cells transiting to S phase at the time of DNA addition, a reaction condition that increases the frequency of gene editing (Brachman & Kmiec, 2005, DNA Repair (Amst). 4:445-57; Engstrom & Kmiec, 2008, Cell Cycle 1402-1414; Liu et al., 2003, Nat. Rev. Genet. 4:679-89). The reaction is initialized by strand invasion of the ssODN into the target duplex with subsequent alignment in homologous register with the target site (here, the mutant eGFP gene) except for a single base pair mismatch located in the center of three-stranded, D-loop structure (Drury et al., 2003, Nucleic Acids Res. 31:899-910). FIG. 1B illustrates the alignment of the ssODN, 72 bases in length (SEQ ID NO: 1), with the appropriate strand of the mutant eGFP gene (SEQ ID NO: 3)

with the consensus 3' to 5' polarity. Previous data suggest that an oligonucleotide of opposite polarity leads to a marked reduction in gene editing activity where the objective is point mutation repair (Strouse et al., 2014, Sci. Rep. 4:3791, Bialk et al., 2015, PLoS One 10:e0129308, Rivera-Torres et al., 2014, PLoS One 9:e96483).

Figure 2:
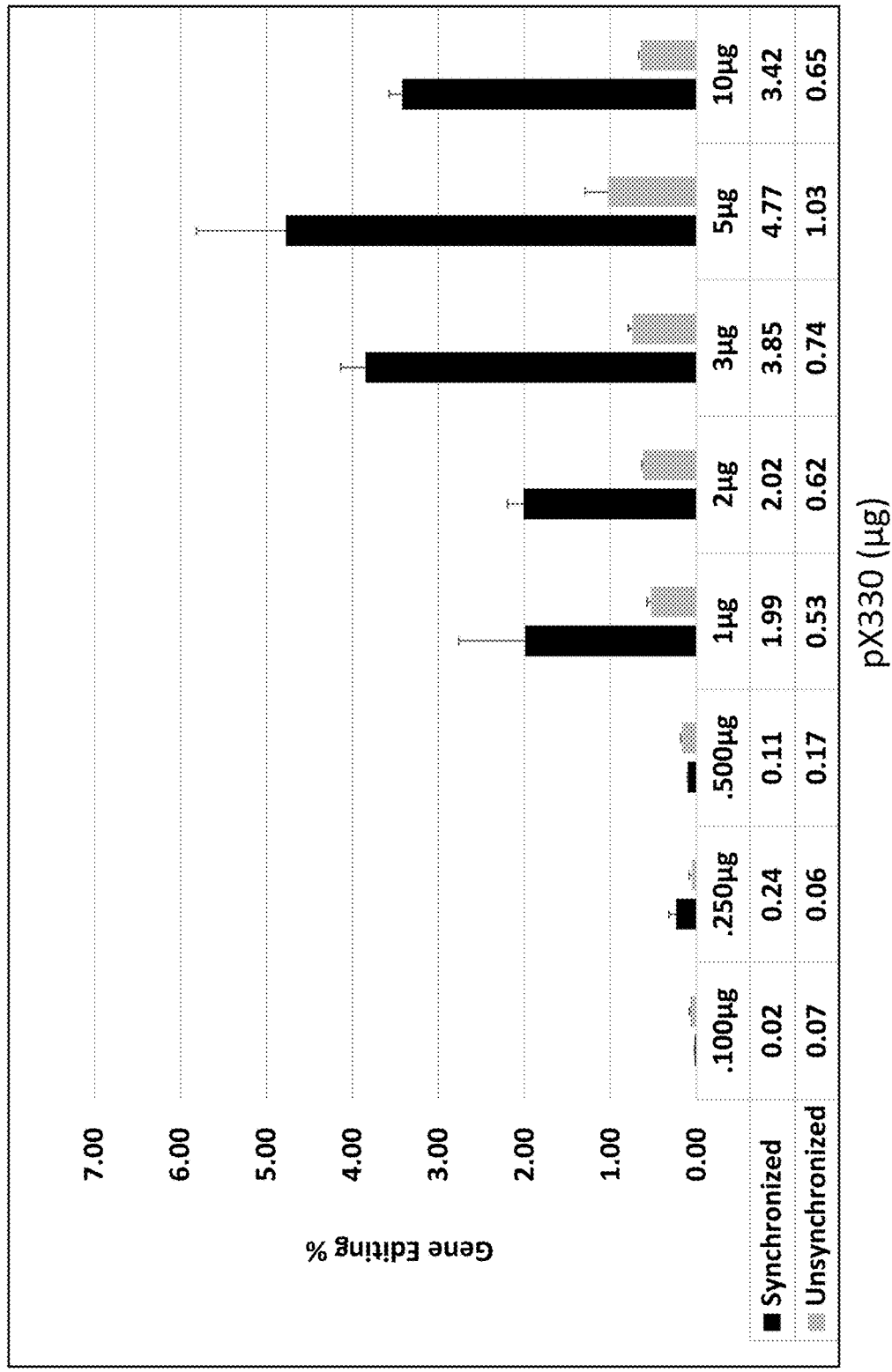
FIG. 2 is a graph illustrating a gene editing dose curve using synchronized and unsynchronized cells. Synchronized (black) and unsynchronized (grey) HCT116-19 cells were electroporated with 0.1-10.0 µg of pX330 and 1.35 µg of 72NT. After a 48-hour recovery period, gene editing activity was measured using a GUAVA EASYCYTE 5HT® (Millipore) multiparameter flow cytometer. Gene editing is displayed as correction efficiency (%), determined by the number of viable eGFP positive cells, divided by the total number of viable cells in the population. Each treatment was performed in triplicate and standard error is illustrated with accompanying bars.

The single-stranded oligonucleotide illustrated in FIG. 1B was combined with a CRISPR/Cas9 system previously designed for the same target (Hu et al., 2005, Mol. Biotechnol. 29:197-210, Bialk et al., 2015, PLoS One 10:e0129308), to examine gene editing activity in mammalian cells from a different perspective. CRISPR/Cas9 cleavage activity was measured using the well-known Surveyor Assay (see Vouillot et al., 2015, G3 (Bethesda) 5:407-15) as well as a recently developed RFLP assay (Rivera-Torres et al., 2014, PLoS One 9:e96483). The oligonucleotide invades the helix with a strict polarity requirement, pairing with its complement in a 3'-5' direction. Using this strategy, gene editing or gene correction takes place via mismatch repair or through incorporation of the ssODN into a replicating daughter strand (Parekh-Olmedo et al, 2006, Gene Ther. 12:639-646; and Radecke et al., 2006, J. Gene Med 8:217-228) specific for the oligonucleotide oriented 3' to 5'. The 72 base ssODN (72-mer) and the CRISPR/Cas9 expression construct were introduced by electroporation and eGFP expression measured 48 hours later by FACS. In the first experiment, the amount of single-stranded oligonucleotide was fixed and the level of CRISPR/Cas9 expression construct was increased in a stepwise fashion. FIG. 2 illustrates the gene editing activity obtained from populations of cells that have either been synchronized and released or unsynchronized prior to the addition of the ssODN and sgRNA/Cas9: pX330. Activity was dose-dependent exhibiting higher levels when the targeted cells have been synchronized and released. Activity was reduced when higher levels of the expression constructs were added due, in all likelihood, to DNA access and extensive DNA cleavage activity.

Figure 3:
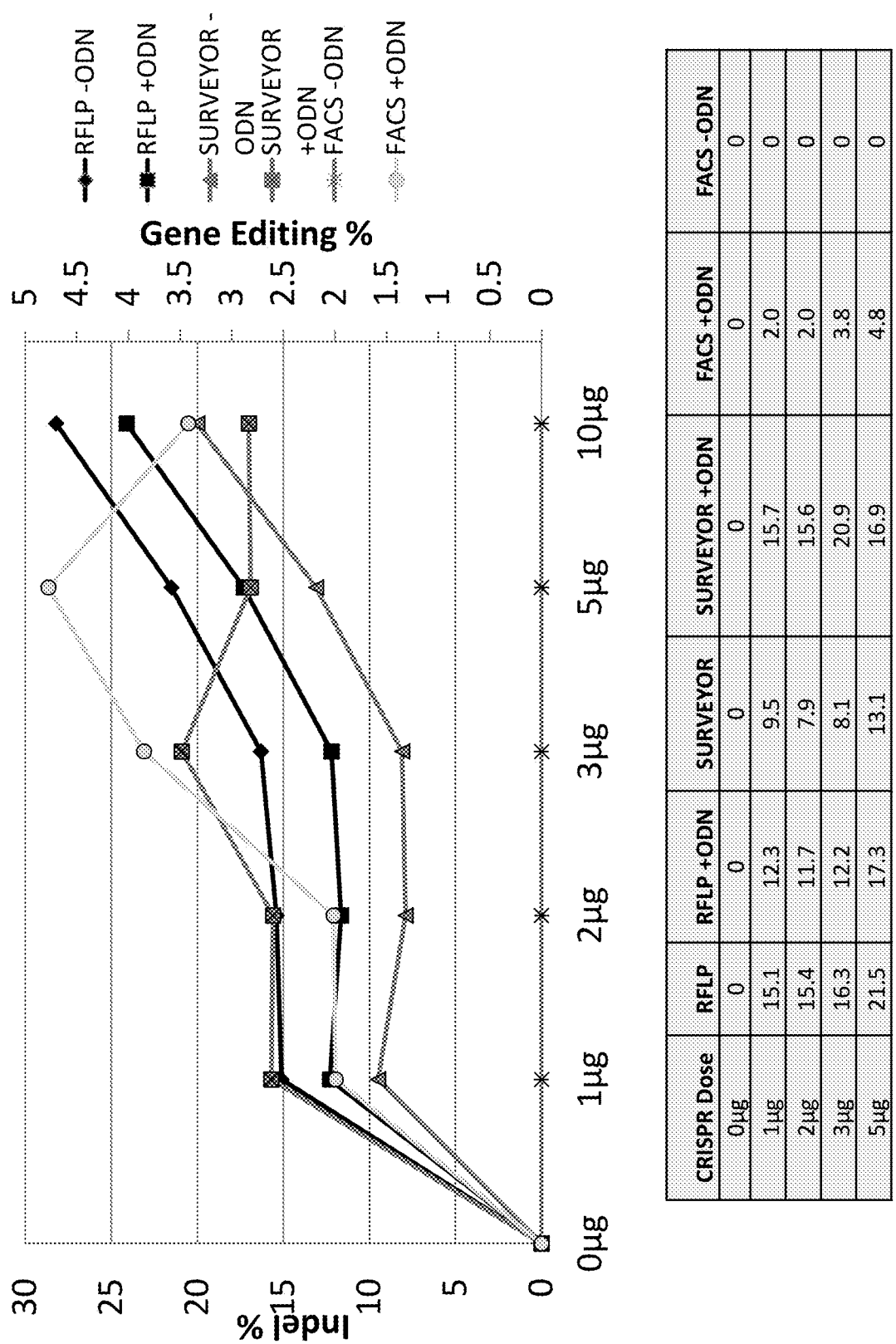
FIG. 3 is a graph illustrating CRISPR/Cas9 activity as measured by SURVEYOR MUTATION DETECTION® kits (Integrated DNA Technologies) and restriction fragment length polymorphism analysis (RFLP) vs gene editing as measured by FACS. Synchronized and released HCT116-19 cells were electroporated with 0.0-10.0 µg of pX330 and with (+ODN) or without (−ODN) 1.35 µg of 72NT.

DNA cleavage activity of the CRISPR/Cas9 system was determined by the Surveyor endonuclease and RFLP assays respectively at dosages where gene editing activity was maximal. The data and relationships among the data from each assay are presented in FIG. 3. Both cleavage assays successfully detected CRISPR/Cas9 activity in the absence of the single-stranded oligonucleotide; a predictable rise in activity was observed as a function of the amount of expression vector added to the cells. When cleavage activity was measured in the presence of the oligonucleotide, which is required for productive gene editing, however, the two revealed different results. In the case of the RFLP assay (black lines) the amount of cleavage is reduced, as it should be, if single-stranded oligonucleotide directed gene repair has occurred (the RFLP/AVR II site, is eliminated). The dose response effectively followed the initial plateau and subsequent increase in gene editing activity; these results confirmed single base pair exchange had occurred. In contrast, the addition of the single-stranded oligonucleotide increased Surveyor endonuclease activity (dark grey lines), particularly at the two doses where gene editing activity was maximized. These data showed that the presence of the oligonucleotide increased the population of DNA substrates amenable for recognition and cleavage by the Surveyor endonuclease.

The Surveyor endonuclease requires the generation of cleavable substrates that are created through the denaturation and re-hybridization of a mixed series of amplicons, some containing a mismatch (s) reflecting cleavage activity. When CRISPR/Cas9 constructs are introduced into a cell with the single-stranded oligonucleotide, the heterogeneity of cleavage products generated is reduced, reflecting a slight suppression of DNA resection as a function of nonhomologous end joining activity. Single-stranded oligonucleotides acting at the site to execute single base repair may indirectly limit the degree of indel formation. This explanation is reflected in the enhancement of Surveyor endonuclease activity which is acted upon DNA duplexes bearing small insertions, deletions and single base mismatches as opposed to DNA substrates larger unpaired regions (Voullot et al., 2015, G3 (Bethesda) 5:407-15).

Figure 4A:
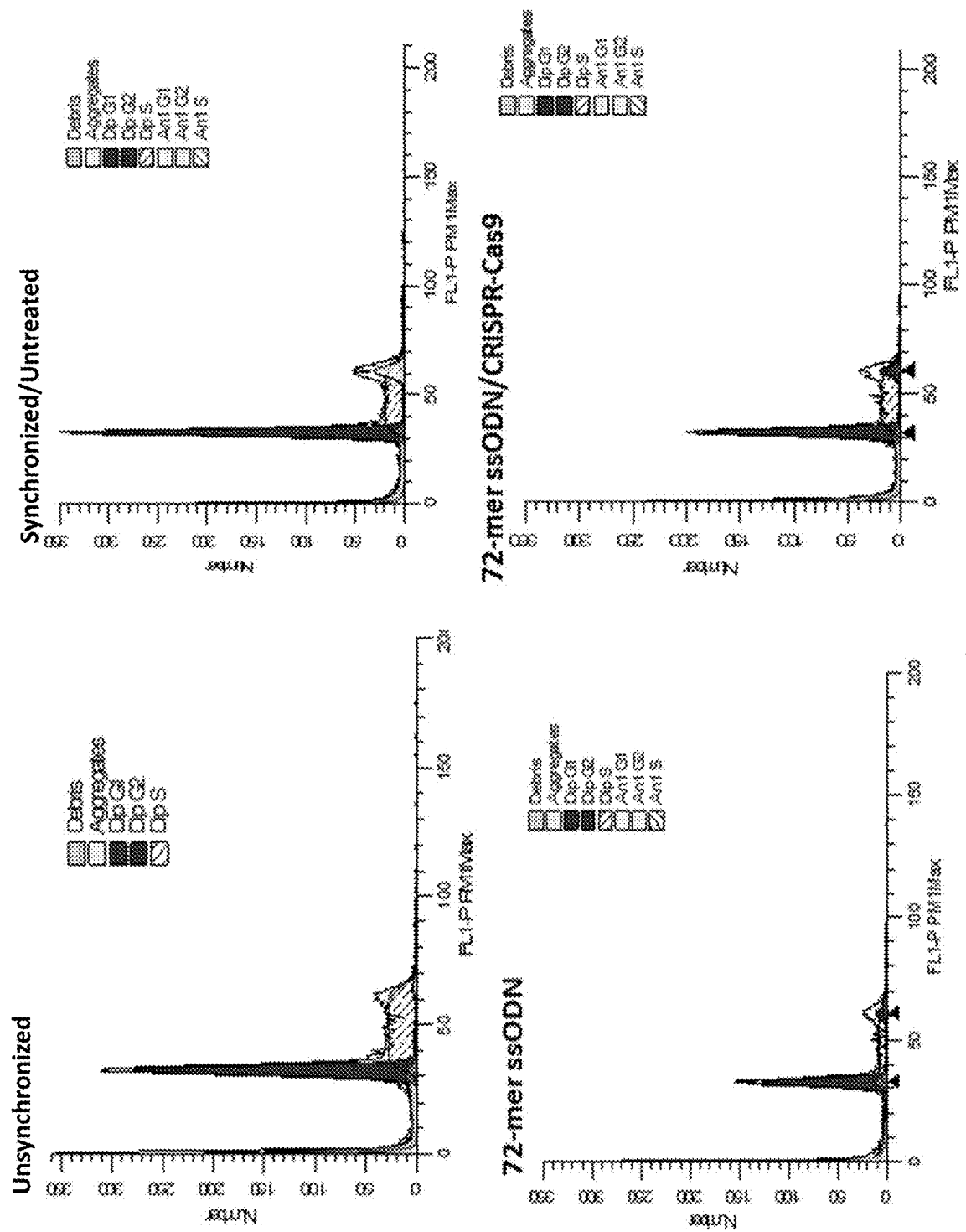
FIG. 4A is a panel of graphs illustrating CRISPR effects on cell cycle progression. HCT116-19 cells were synchronized with 6 µM aphidicolin for 24 hours and released for an additional 4 hours in culturing medium. Synchronized and unsynchronized HCT116-19 cells were simultaneously transfected at a concentration of $5 \times 10^5$ cells/with 1.35 µg single-stranded oligonucleotide and 3 µg CRISPR/Cas9 plasmid constructs. Cells were allowed to recover in complete growth media for 24 hr. Cell cycle profiles illustrate DNA content distributions of the cells at 24 hr post transfection. Cell cycle modeling was performed using the auto analysis feature of the MODFIT LT™ software (Verity Software House). S-phase extension was by Diploid (%), Diploid: S-phase (%), and Total S-Phase (%) (Average S-Phase). Debris (%) was also analyzed to determine the quality of the analyzed data.

The process of single base gene editing in mammalian cells leads to small but detectable slowing of the progression of targeted cells through S phase, perhaps due to the activation of the DNA damage response pathway (Olsen et al., 2009, DNA Repair (Amst) 8:298-308; Ferrara, 2007, DNA Repair (Amst) 6:1529-35; Ferrara et al., 2006, DNA Repair (Amst) 5:422-31; Nur-E-Kamal et al., 2003, J. Biol. Chem. 278:12475-81). This collateral effect enhances gene editing activity as the longer period of time spent in S-phase coordinately extends the open conformation of the chromatin thereby increasing accessibility of the target for the oligonucleotide. But, otherwise the cells exhibit a standard cell cycle profile. The profile of the target cell population was analyzed under conditions that exhibited both significant levels of gene editing activity as well as CRISPR/Cas9 cleavage activity. As seen in FIGS. 4A and 4B, no significant damage to cell cycle progression was observed but an increase in the number of cells progressing through S phase was observed when the single-stranded oligonucleotide was combined with expressed CRISPR/Cas9. An increase in the amount of debris generated under these conditions was also apparent, which may be due to chromosomal degradation as a function of repetitive cleavage activity.

The relationship between DNA cleavage activities, as measured by two established assays, and a gene editing reaction wherein a single-stranded oligonucleotide and CRISPR/Cas9 jointly execute single base repair were investigated. This reaction differed from the broadly used approach where single-stranded oligonucleotides are used to catalyze DNA insertion.

The presence of the single-stranded oligonucleotide enhanced the activity of the Surveyor endonuclease assay by increasing the size of the population of suitable cleavage substrates but reduced the activity of AvrII in the RFLP assay by catalyzing single base exchange through the destruction of the restriction site. These data suggest that correlations between DNA cleavage and gene editing activities can be made albeit cautiously, since the relationship is dependent on the type of genetic or biochemical readout used to measure respective activities. These data demonstrate that single-stranded oligonucleotides themselves are useful in reducing the heterogeneity of DNA ends created through the activity of programmable nucleases and NHEJ.

Figure 11:
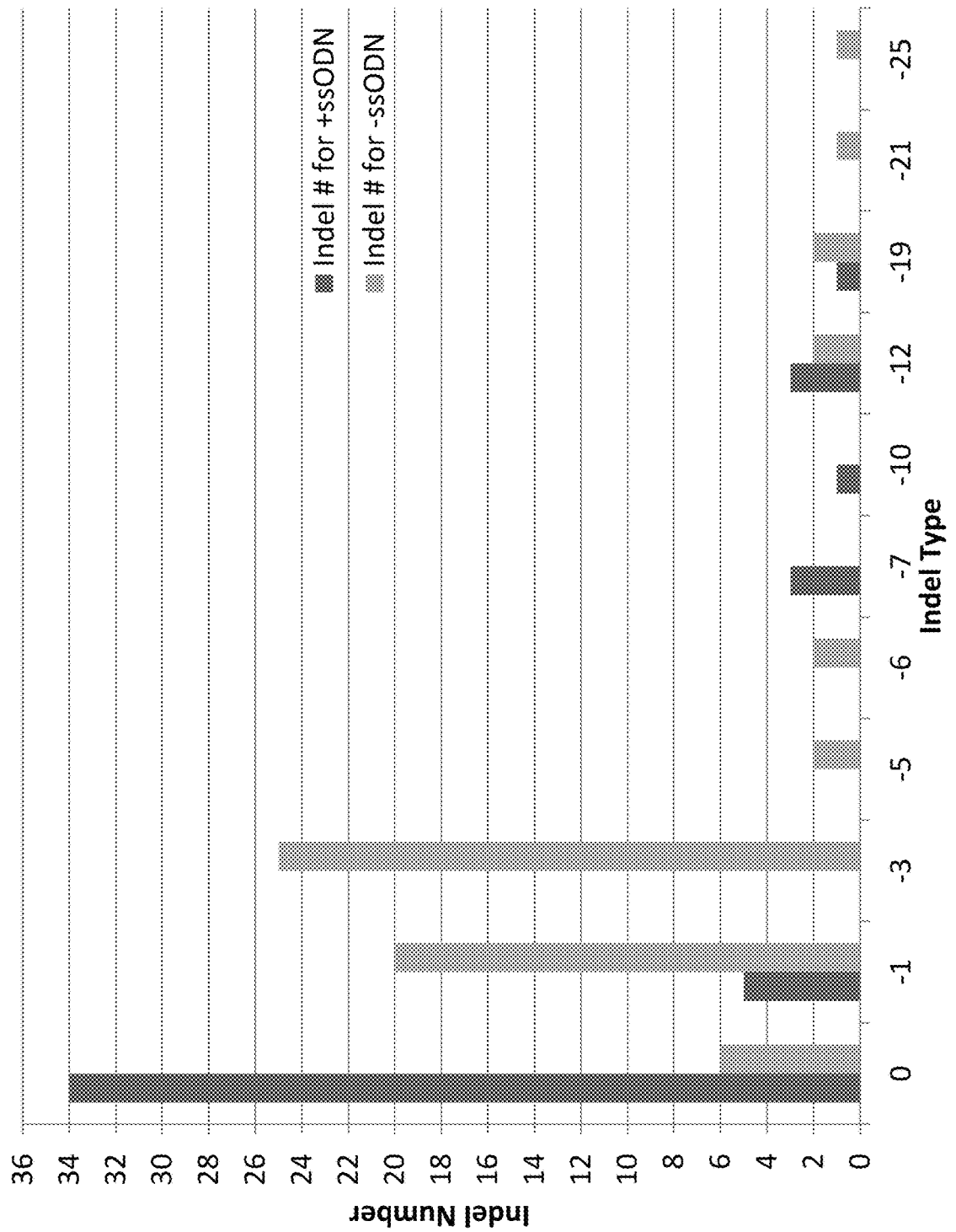
FIG. 11 is a graph showing the distribution of insertions or deletions created by the CRISPR/Cas9 complex in the absence or presence of a single-stranded oligonucleotide. Data was compiled from 108 mammalian cell clonal expansions randomly chosen from experiments involving CRISPR activity on the eGFP gene or the human beta globin gene.

The degree of resection was measured in 108 mammalian cell lines generated as clonal expansions from samples that had been treated with CRISPR/Cas9 in the absence or presence of single-stranded DNA (FIG. 11). This was carried out by isolating genomic DNA from each of these clonal expansions and sequencing across the junction sites where the intended with a crisper target site was designed to operate. By comparing 47 samples from clones generated through the action of CRISPR/Cas9 plus single-stranded DNA oligonucleotides and 61 samples from clones generated through the action of CRISPR/Cas9 alone i.e. in the absence of single-stranded DNA oligonucleotides, a distinct reduction in the extent of insertions or deletions (indels)

found as a result of the resection activity at the cleavage site was observed. These data were generated by carrying out DNA sequence analysis by primer spanning the junction site, DNA PCR products of approximately 600 bases in length. These data demonstrate that the presence of single-stranded DNA oligonucleotides in a gene editing reaction catalyzed by CRISPR/Cas9 reduces the degree of mutagenicity at or surrounding the target site, as reflected in the lower number of indels created during reactions containing the single-stranded DNA oligonucleotide.

Example 2: Insertional Mutagenesis by CRISPR/Cas9 Ribonucleoprotein Gene Editing in Cells Targeted for Point Mutation Repair Directed by Short Single-Stranded DNA Oligonucleotides Single-stranded DNA oligonucleotides (ssODNs) can act as templates for the repair of point mutations in human cells. These molecules direct nucleotide exchange at precise positions and without detectable off target effects. While there is great utility in single agent gene editing, the frequency with which single base repair takes place has been consistently lower than needed for long-term development. The mechanism and regulation of single agent gene editing, however, has been elucidated and based on these studies two important enhancers of the frequency have been uncovered. The first involves double strand DNA breakage induced by the activity of anticancer drugs such as Camptothecin or VP16, etc in a process that leads to the activation of pathways involved in DNA damage response. The second method of increasing the frequency of point mutation repair involves the modulation of the cell cycle. Synchronization of cells at the G1/S border followed by release, generates a population of cells that are more amenable to gene repair thereby increasing correction frequency by 5 to 10 fold.

RNA guided engineered nucleases (RGENs) particularly CRISPR/Cas9 systems, can elevate the frequency of point mutation repair when used in combination with single-stranded DNA oligonucleotides. By and large, the mechanism and regulation of combinatorial gene editing are similar to the pathways described for single agent gene editing, enhanced by the manipulation of the cell cycle prior to targeting. While this approach has generated a considerable and understandable level of excitement in the field, there are concerns that CRISPR/Cas9 activity, dependent upon or independent from ssODNs, could result in off-site or onsite mutagenesis as a function of its normal mechanism of action. Since CRISPR/Cas9 induces a double strand break that then becomes the template for nonhomologous end joining, it is likely that a heterogeneous population of chromosomal ends is created in corrected and uncorrected cells, particularly at the target site. Intense effort is being placed on developing CRISPR/Cas9 variants that inherently reduces the capacity to target off-site. Since the active complex of CRISPR/Cas9 consists of RNA and protein, one approach is to target cells with a pre-formed Ribonucloprotein (RNP) complex that, due to a shorter half-life within the cell, may exhibit nonspecific mutagenesis.

Recently, a population of cells bearing a single base change induced by the combination of CRISPR/Cas9 and ssODNs for altered DNA sequence of the beta globin gene was analyzed. The findings indicated that point mutation repair directed by these gene editing tools leaves a mutagenic footprint. Both insertions and deletions accompanied single base repair as judged by allelic analysis of clonally expanded cell populations. The type of DNA heterogeneity created at the site of single base repair was investigated in both corrected and uncorrected cell populations in more detail. A human cell model system containing a mutant eGFP gene that upon correction enables a simple phenotypic readout that can be confirmed by DNA analysis. The mutant eGFP contains a single point mutation that switches a codon for tyrosine (TAC) to a stop codon (TAG). Correction of the stop codon reestablishes the tyrosine codon and rescues the phenotype generating functional eGFP that can be readily measured by FACS. This useful and robust system was used to examine point mutation repair and the associated collateral damage created in corrected and uncorrected cells. Targeted cells and expanded clonal populations were isolated for DNA sequence analysis. Cells bearing a corrected eGFP gene exhibited no collateral damage and no onsite mutagenesis. In contrast, some of the expanded clones from populations of targeted cells in which no phenotypic change was observed, exhibited intact mutant sequences without associated modifications, while others exhibited a wide range of indel formation, including insertional mutagenesis in the creation of hybrid genes encoding truncated proteins. These results provide the basis for a new model of gene editing for point mutations and emphasize the importance of evaluating all cells targeted for gene editing by CRISPR/Cas9 and ssODNs, especially as gene editing extends toward human therapy.

The materials and methods employed in these experiments are now described.

Cell Line and Culture Conditions: HCT 116 cells were acquired from ATCC (American Type Cell Culture, Manassas, Va.). The HCT 116-19 was created by integrating a pEGFP-N3 vector (Clontech, Palo Alto, Calif.) containing a mutated eGFP gene. The mutated eGFP gene has a nonsense mutation at position +67 resulting in a nonfunctional eGFP protein. For these experiments, HCT 116-19 cells were cultured in McCoy's 5A Modified medium (Thermo Scientific, Pittsburgh, Pa.) supplemented with 10% fetal bovine serum, 2 mM L-Glutamine, and 1% Penicillin/Streptomycin. Cells were maintained at 37° C. and 5% $CO_2$. The eGFP targeting custom designed 72-mer oligonucleotide was synthesized by IDT (Integrated DNA Technologies, Coralville, Iowa).

CRISPR/Cas9 RNP Design and Complexing: The mutant eGFP gene sequence was entered into the Zhang Lab's online generator (crispr dot mit dot edu) and the CRISPR guide sequences which binds with close proximity to target (TAG=0) was chosen. crRNA, tracrRNA and Cas9 protein were kind gifts from Integrated DNA Technologies (Coralville, Iowa) and stored and utilized according to their suggestions. RNP assembly was performed by mixing RNA oligos (crRNA and tracrRNA) in equimolar concentrations to a final duplex concentration of 45 μM. For the RNA to duplex the mix was heated at 95° C. for 5 minutes and allowed to cool to room temperature (15-25° C.). For each sample crRNA:tracrRNA (45 μM working solution) and Cas9 protein (60 μM stock solution) were diluted in their respective buffers to a final volume of 5 μL each to achieve the desired treatment concentration. Prior to mixing with cells crRNA:tracrRNA duplex and Cas9 protein we mixed and set to incubate at room temperature for 15 minutes. The same annealing conditions and reactions were carried out in the assembly of the mutant eGFP or B-globin gene crRNA (28) RNP.

Experimental Strategy: For all experiments, HCT 116-19 cells were synchronized for 24 hours with Aphidicholin at the G1/S border prior to introducing the Cas9 ribonucleoprotein (RNP) complex or CRISPR/Cas9 generated from an expression construct. The CRISPR expression plasmid was constructed using standard cloning methods following the latest oligo annealing and backbone cloning protocol with single-step digestion-ligation. The CRISPR guide sequences were cloned into the pX330 backbone vector (Addgene plasmid 42230), a human codon-optimized SpCas9 and chimeric guide RNA expression plasmid. Single-stranded DNA oligonucleotides used in this study are 72 base pairs in length and designed as depicted in FIG. 5. RNP assembly was performed by mixing RNA oligos (crRNA and tracrRNA) in equimolar concentrations to a final duplex concentration of 45 µM. For the RNA to duplex the mix was heated at 95° C. for 5 minutes and allowed to cool to room temperature (15-25° C.). For each sample crRNA:tracrRNA (45 µM working solution) and Cas9 protein (60 µM stock solution) were diluted in their respective buffers to a final volume of 5 µL each to achieve the desired treatment concentration (24-120 pmol). Prior to mixing with cells crRNA:tracrRNA duplex and Cas9 protein we mixed and set to incubate at room temperature for 15 minutes. Electroporation transfection was performed by mixing cells at concentration of $5 \times 10^5$ cells/100 microliters along with the RNP and ssODNs in a 4 mm gap cuvette (BioExpress, Kaysville, Utah) (250V, LV, 13 ms pulse length, 2 pulses, is interval) using a Bio-Rad Gene Pulser™ XCell Electroporation System (Bio-Rad Laboratories, Hercules, Calif.). Cells were then recovered in 6-well plates with complete growth media at 37° C. for 72 hours prior to analysis.

Analysis of Gene Edited Cells and Transfection Efficiency: HCT 116-19 cell fluorescence (eGFP+) was measured by a BD FACSAria II (BD Biosciences, San Jose, Calif.). Cells were harvested by trypsinization, washed once with 1×PBS (−/−) and resuspended in buffer (0.5% BSA, 2 mM EDTA, 2 µg/mL Propidium Iodide in PBS−/−). Propidium iodide was used to measure cell viability as such, viable cells stain negative for PI (uptake). Correction efficiency was calculated as the percentage of the total live eGFP positive cells over the total live cells in each sample. Error bars are produced from three sets of data points generated over three separate experiments using basic calculations of Standard Error.

RNP in vitro activity: Cellular gDNA was isolated from pellets of $1 \times 10^6$ untreated HCT 116-19 cells using Qiagen DNAEasy Blood and Tissue Kit (Cat. ID 69506, Valencia, Calif.). PCR was performed using AmpliTaq (Thermo-Scientific, Waltham, Mass.) on 200 ng of isolated gDNA, with amplification parameters optimized for an amplicon size of 605 bp with forward primer 5'-CTGGACGGCGACGTAAACGGC-3' (SEQ ID NO: 4) and reverse primer, 5'-ACCATGTGATCGCGCTTCTCG-3' (SEQ ID NO: 5). Amplicon size was verified on 1% agarose gel and PCR samples were cleaned up using the QIAquick PCR purification kit (Qiagen, Hilden, Germany). After purification, 300 ng of PCR sample was combined with Buffer 3.1 and 25 pmols or 50 pmols of RNP complex. The mix was incubated for 40 minutes at 37° C. then 1 microliter of proteinase K was added to the mix and incubated for 15 minutes. Samples were loaded along with NEB 2-log DNA ladder (NEB, Ipswich, Mass.) and analyzed on a 2% TBE agarose gel.

Cellular gDNA was isolated from pellets of $1-2 \times 10^6$ K562 cells using the Qiagen DNEasy Blood and Tissue Kit (Cat. ID 69506, Valencia, Calif.). PCR was performed using Phusion High-Fidelity PCR Master Mix with HF Buffer (Thermo-Scientific, Waltham, Mass.) on isolated gDNA, with amplification parameters optimized for an amplicon size of 345 bp with forward primer 5'-TCCTAAGCCAGTGCCAGAAGAG-3' (SEQ ID NO: 6) and reverse Primer 5'-CTATTGGTCTCCTTAAACCT-3' (SEQ ID NO: 7). Amplicon size was verified on 1% agarose gel. PCR samples were cleaned up using the QIAquick PCR purification kit (Qiagen, Hilden, Germany) and treated with DdeI restriction enzyme (NEB, Ipswich, Mass.) following the manufacturer's protocol or RNP following the method described above. Digested samples were loaded along with NEB 2-log DNA ladder (NEB, Ipswich, Mass.) and analyzed on a 2% TBE agarose gel.

DNA sequence analysis: Synchronized and released HCT 116-19 cells were harvested and electroporated at a concentration of $10^5$ cells/100 microliters with RNP complex at 100 pmols and 72NT ODN at 2.0 micromolar. Following electroporation, cells were placed in 6-well plates and allowed to recover for 72 hours. Cells were then individually sorted by a BD FACSAria II sorter—488 nm (100 mw) (BD Biosciences, San Jose, Calif.) for eGFP+/− into 96-well plates. Cells were expanded over 6 weeks and harvested. Cellular gDNA was isolated using Qiagen DNEasy Blood and Tissue Kit (Cat. ID 69506, Valencia, Calif.) and the region surrounding the target base was amplified via PCR (718 bp, forward primer 5'-ATGGT-GAGCAAGGGCGAGGA-3' (SEQ ID NO: 8) and reverse primer 5'-ACTTGTACAGCTCGTCCATGC-3'(SEQ ID NO: 9)). Samples were submitted to Eton Bio Incorporated (Union, N.J.) for sequencing analysis.

Results of the experiments are now described.

FIG. 5 displays part of the sequence of the mutant eGFP gene that has been inserted as a single copy into HCT 116 cells and driven by a CMV promoter to generate the cell line HCT 116-19. The underlined point mutation target is the terminal base of the TAG stop codon. Gene editing using CRISPR/Cas9 and ssODNs aims to rescue the mutation, converting the G base to a C and restoring the normal tyrosine codon (TAC). The wild type eGFP sequence is depicted as is the sequence of the 72 base single-stranded oligonucleotide, which is complementary to the non-transcribed (non-template) strand (72NT). Also included in the figure is the sequence of the protospacer and the PAM sequence as well as the sequence of the mutant gene. This specific combination of CRISPR/Cas9 and ssODN is optimal for RGEN-directed correction. In the experiments reported herein, the 72NT oligonucleotide was utilized since targeting the non-transcribed strand at this ssODN length leads to a higher level of gene editing. In addition, the use of the complementary oligonucleotide, targeting the transcribed strand, leads to artefactual annealing to the sgRNA component of the CRISPR/Cas9 complex, reducing overall activity. Successful correction of the point mutation leads to the production of a functional eGFP which can be detected and quantified by FACS.

Figure 6A:
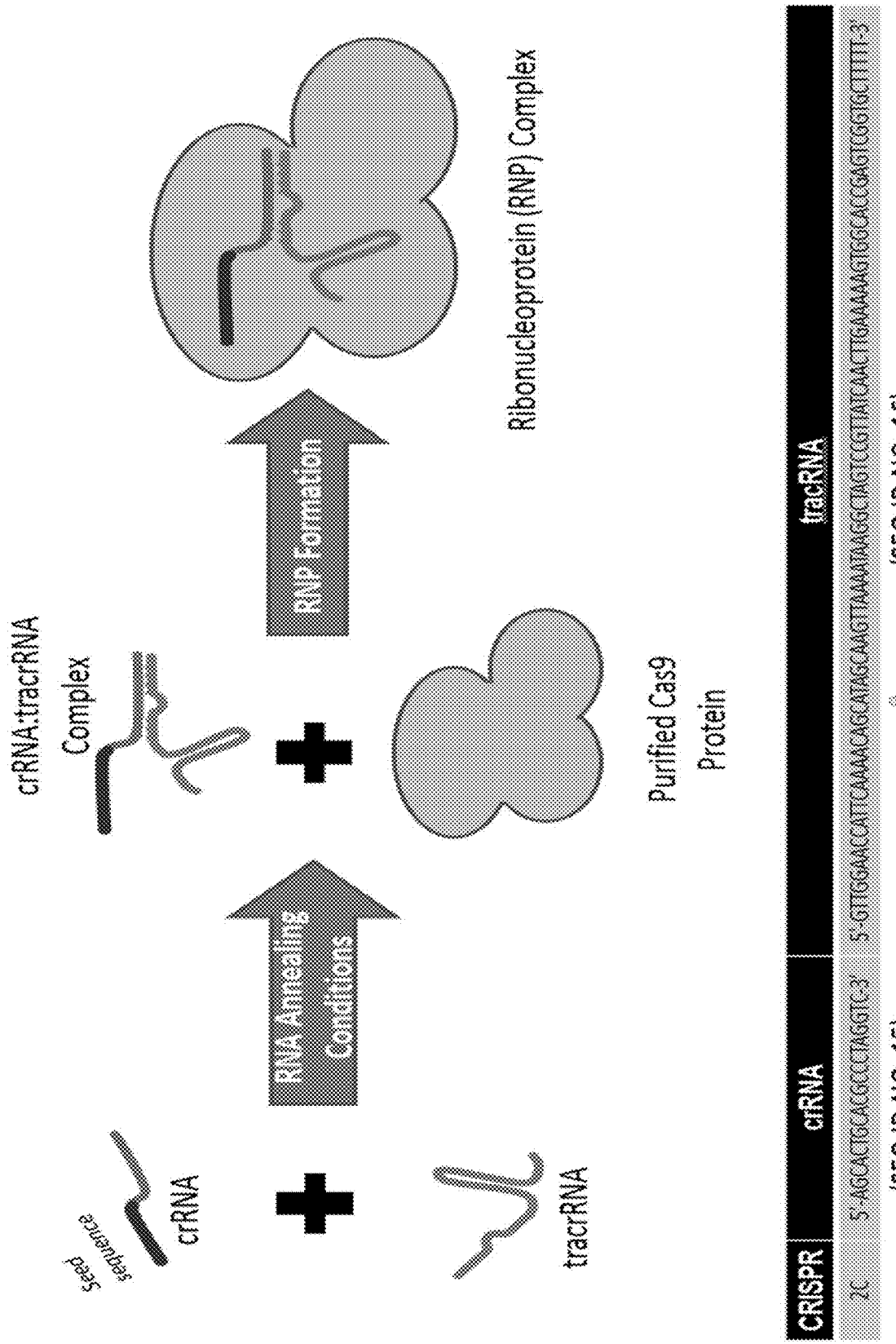
FIG. 6A illustrates CRISPR/Cas9 Ribonucleoprotein Assembly Reaction. crRNA provides target specificity (20 bases) corresponding to the 2C protospacer sequence and an interaction domain with the tracrRNA. crRNA and tracrRNA are annealed in equimolar concentrations. Cas9 protein (gray) is added to complete RNP assembly. Guide RNAs (gRNAs) direct and activate the Cas9 endonuclease which then cleaves the target DNA. The lower section of the figure shows the 2C seed sequence and the tracrRNA sequence.
Figure 6B:
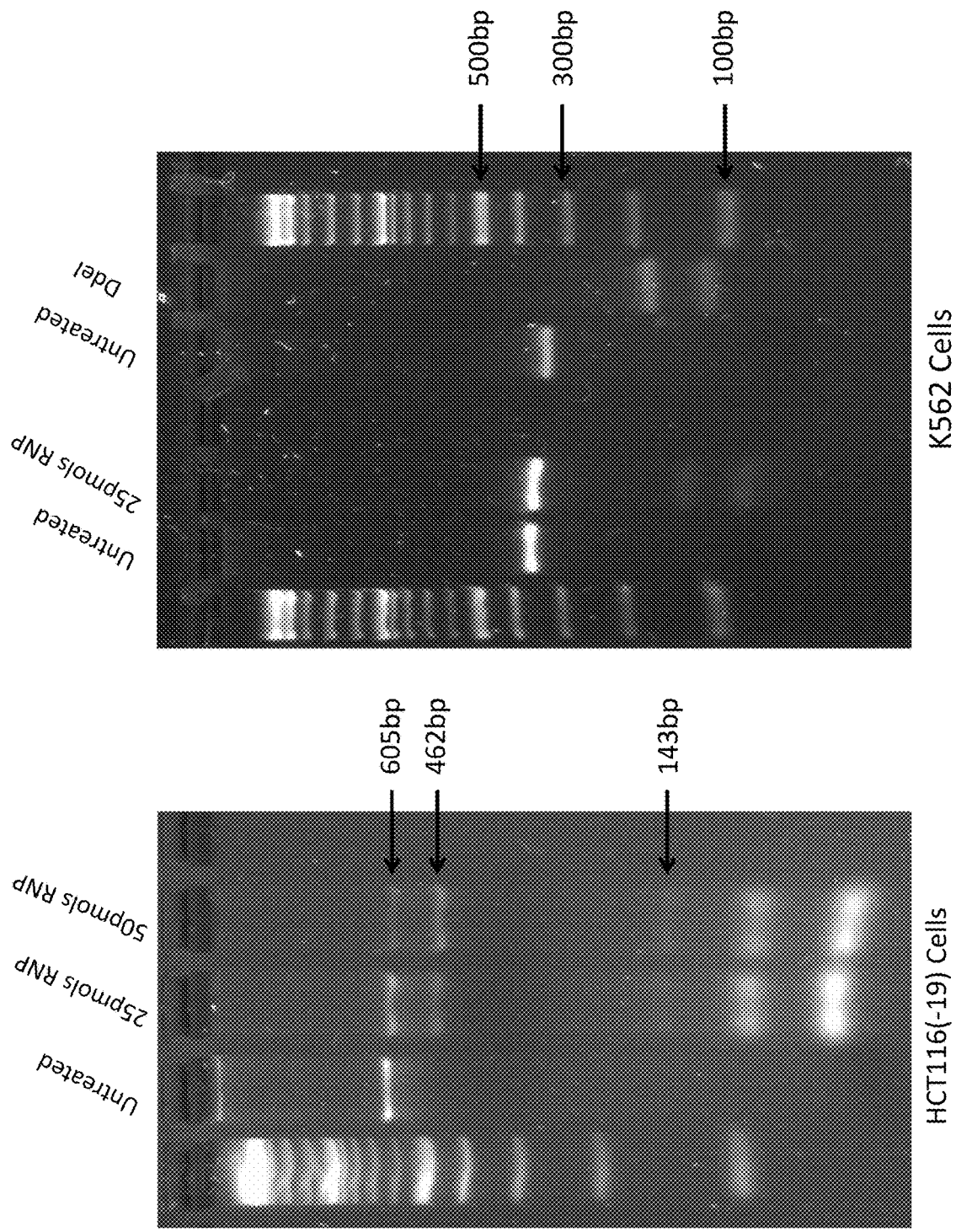
FIG. 6B illustrates in vitro RNP Digestion. Genomic DNA was isolated from untreated HCT 116-19 cells and PCR used to generate an amplicon of size 605 bp, which surrounds the sequence of the integrated mutant eGFP gene. The amplicon was combined with 25 pmols and 50 pmols of RNP complex respectively, and incubated for 40 minutes at 37° C. In the complete reaction, two products were generated with sizes consistent with fragments predicted from the specific cut site designed for the RNP complex. As a control, the RNP complex was incubated with an amplicon generated from the HBB gene 345 base pairs in length from cell line K562. A control digest was performed on the 345 base amplicon with the restriction enzyme DdeI

Both components (sgRNA and Cas9) can be generated from a plasmid expression vector. In this study, however, the CRISPR/Cas9 was provided as a ribonucleoprotein complex that is preassembled prior to introduction into the cells. FIG. 6A provides a schematic of the assembly process. The crRNA and the tracrRNA are identical in sequence to the longer sgRNA used previously although they are used as separate RNA molecules in this protocol. The crRNA and tracrRNA were reannealed by mixing RNA oligos (crRNA and tracrRNA) in equimolar concentrations with subsequent addition of purified Cas9 protein. To measure inherent activity of the RNP with regard to its capacity to cleave DNA, an in vitro reaction was carried out that assessed the capacity of this particular RNP complex to induce double strand DNA cleavage in a specific fragment of DNA. The fragment was created by PCR amplification across the mutant eGFP target site generating a 605 base pair template containing the target site for the RNP. The preassembled RNP was mixed with this fragment at various concentrations for 40 minutes followed by deproteinization by Proteinase K. The digestion fragments were visualized after gel electrophoresis and the data are presented in FIG. 6B. The RNP efficiently catalyzes double strand DNA cleavage of the specific fragment but not of a fragment lacking the target site. These results support the notion that the RNP complex assembled under our reaction conditions contains the appropriate level of activity and specificity for inducing double strand DNA cleavage.

Figure 7A:
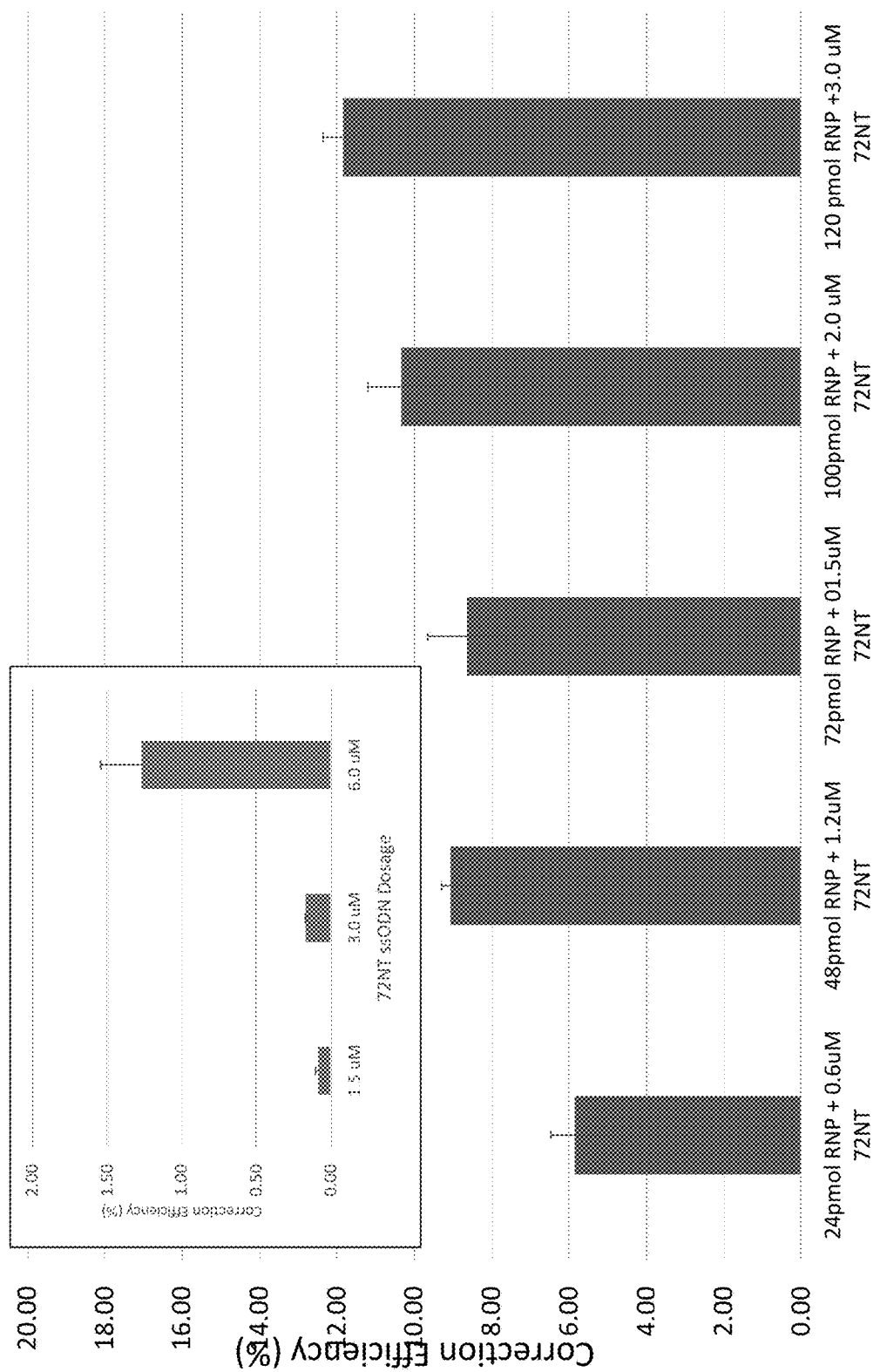
FIG. 7A illustrates the finding that gene editing is dose dependent when directed by the RNP and the ssODN. Synchronized and released HCT 116-19 cells were electroporated with 24-120 pmol CRISPR/Cas9 RNP and 0.6-3.0 µM of 72 mer. After a 72-hour recovery period, gene editing activity was measured using a FACSAria II flow cytometer. Gene editing is displayed as correction efficiency (%), determined by the number of viable eGFP positive cells divided by the total number of viable cells in the population. Each treatment was performed in triplicate and standard error is illustrated with accompanying bars. Inset: Single agent gene editing. Gene editing activity directed by the single-stranded oligonucleotide (72NT) in the absence of the RNP complex under identical conditions is presented as a function of increasing concentration.
Figure 7B:
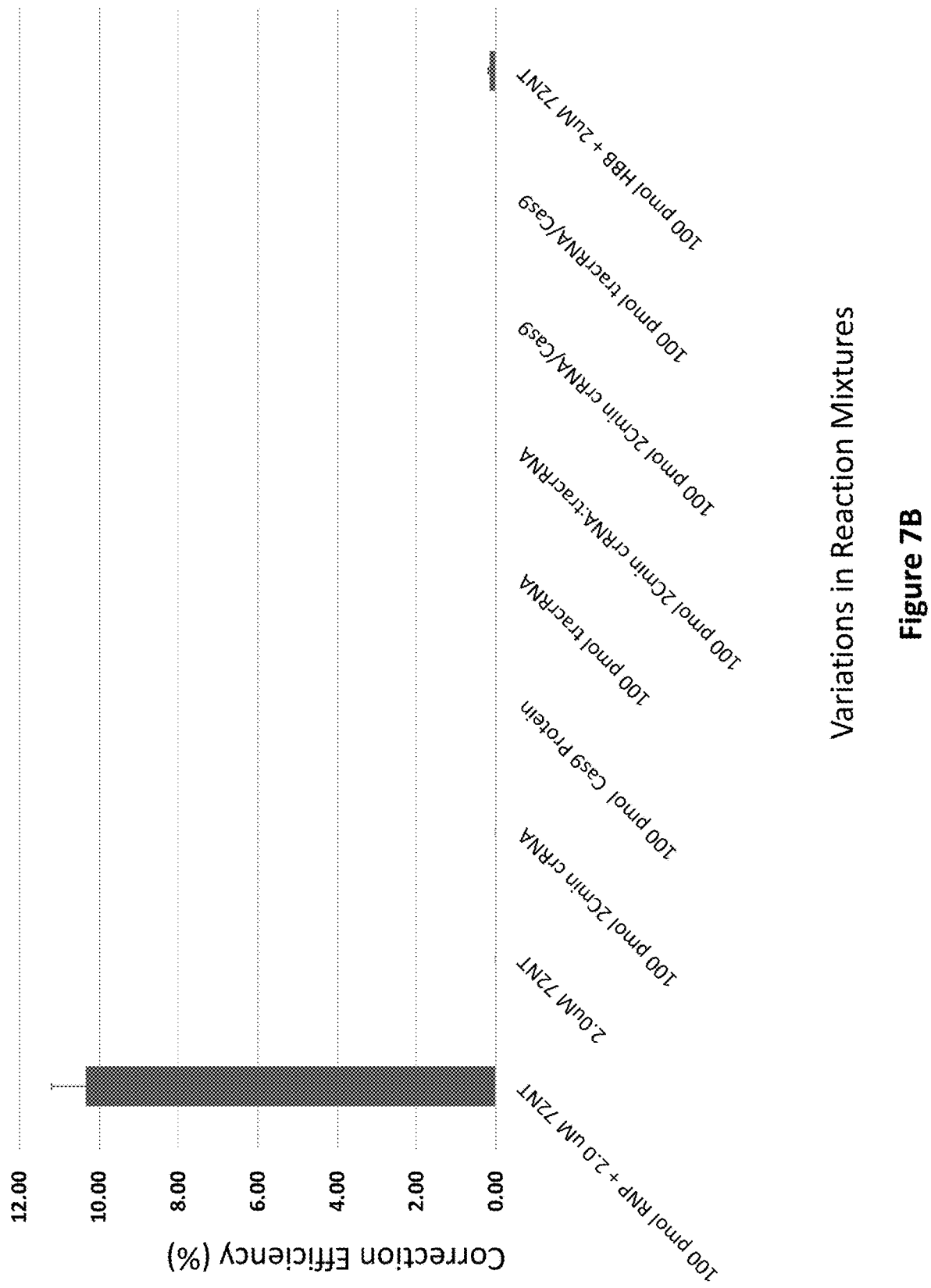
FIG. 7B illustrates the finding that gene editing activity is dependent on all components being present in the reaction mixture. Synchronized and released HCT 116-19 cells were electroporated with 100 pmol of the crRNA, Cas9 Protein, tracrRNA and 2.0 µM of the 72NT, as a complete reaction. Identical mixtures, lacking the indicated reaction component, were carried out in parallel. In one specific reaction mixture, the RNP specific for the beta globin gene replaced the RNP specific for the eGFP gene (far right bar). After a 72 hour recovery period, gene editing activity was measured using a FACSAria II flow cytometer. Gene editing is displayed as correction efficiency (%), determined by the number of viable eGFP positive cells divided by the total number of viable cells in the population. Each treatment was performed in triplicate and standard error is illustrated with accompanying bars.

For the cell-based gene editing reaction, the RNP was combined with 72NT at a prescribed molar ratio of 1:2.5 and immediately electroporated into HCT 116-19 cells. Cells were allowed to incubate for 72 hours after which time they were processed for FACS analysis. A dose curve was carried out with increasing concentrations of the preassembled RNP, while maintaining a constant ratio of ssODN (72NT) to RNP. The data are presented in FIG. 7A and exhibit a steady increase in correction efficiency, rising steadily from the initial level of 24 pmols of RNP to a high level when 120 pmols are used in the reaction. In contrast, single agent gene editing using only the 72NT produced a much lower level of gene editing. These data suggest that the RNP particle used in combination with the 72NT oligonucleotide can promote gene correction at a level approaching 10 to 12% reproducibly. The next experiment addresses the question of the importance of each reaction component. A complete reaction mixture was utilized containing 100 pmol of RNP complex and 2.0 μM of 72NT respectively. As shown in FIG. 7B, elimination of one or two of the essential reaction components eliminated gene editing activity completely. In addition, a complete reaction mixture was tested for activity after replacing the specific RNP complex with one that targets the beta globin gene. No reproducible levels of gene editing were observed emphasizing the requirement for the specific RNP particle coupled to the single-stranded oligonucleotide to direct correction of the point mutation in the eGFP gene. The reaction mixture containing all of the relevant components, however, promoted correction efficiency of approximately 10% (FIG. 7A). This level of gene editing directed by the RNP/72NT complex can therefore produce a sufficient level of eGFP positive cells separated from eGFP negative cells to enable robust single cell sorting by FACS and subsequent clonal expansion.

Figure 8A:
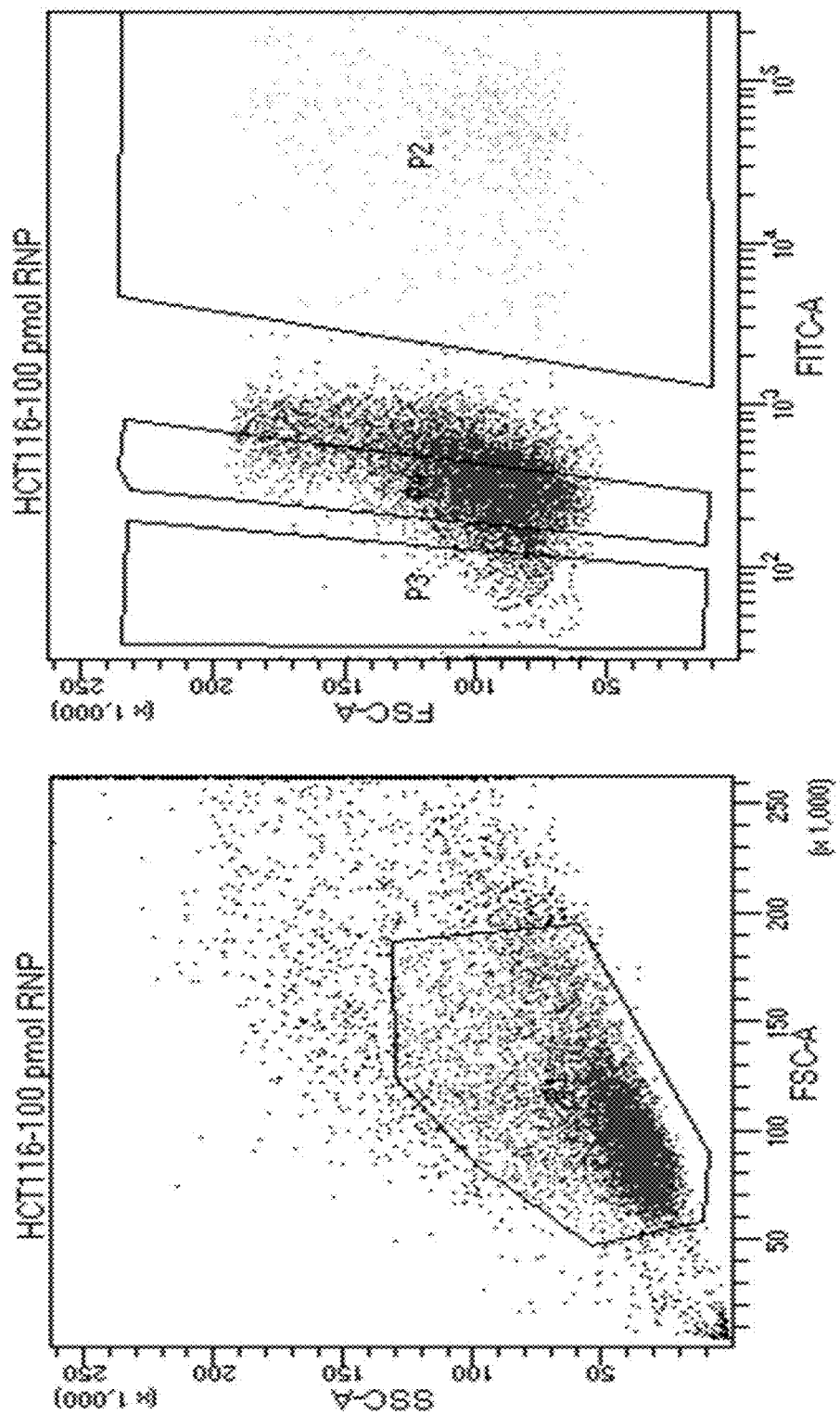
FIG. 8A illustrates FACSAria II plots of gene editing activity in HCT 116-19 cells. HCT 116-19 cells synchronized for 24 hours at the G1/S border and released were electroporated with 100 pmol of RNP complex and 2.0 µM of the 72NT ssODN. After 72 hours, the cells were analyzed using FACS and single cells were sorted individually into 96-well plates. Two distinct populations were collected. The population of live, eGFP-positive cells (labeled as P2 on the FACS plot) as well as the population of live, eGFP-negative cells (labeled as P3) were segregated into separate clonal expansion plates.
Figure 8B:
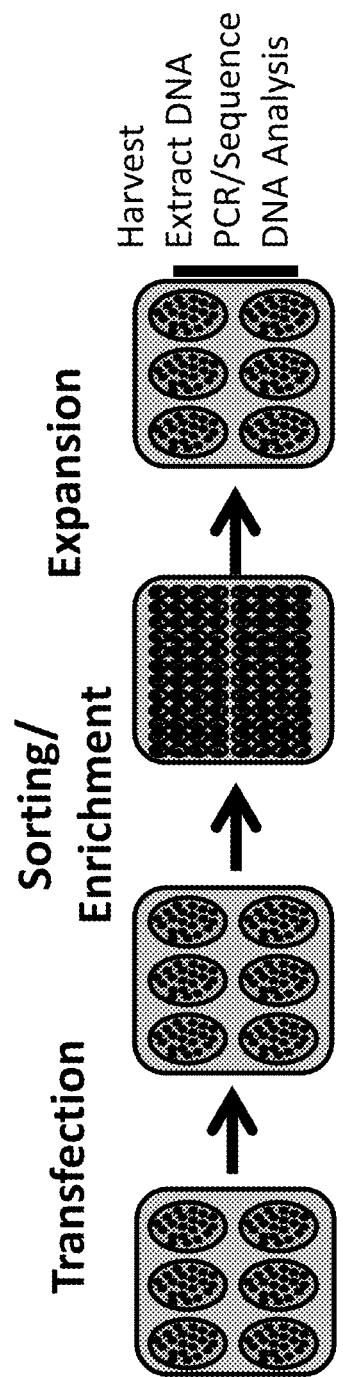
FIG. 8B illustrates experimental strategy isolation of single cell clones. Cells exhibiting eGFP expression were scored positive and sorted using a FACSAria II flow cytometer as single cells into individual wells for clonal expansion. Cells lacking eGFP expression isolated and sorted in a similar fashion and expanded under the same conditions. DNA was then isolated and the eGFP gene was amplified and subjected to Sanger sequencing to analyze gene editing activity surrounding the target site.

FIG. 8A presents a side scatter plot of a complete gene editing reaction on a population of HCT 116-19 cells. The segmented plot illustrates a distinct percentage of cells in the P2 quadrant, representing eGFP positive cells that can be distributed as individual cells into a single well of a 96 well plate. In a similar fashion, uncorrected cells from the population displayed in quadrant P3 can also be isolated. FIG. 8B displays the experimental flow following transfection and sorting, enrichment and finally clonal expansion prior to DNA harvesting, extraction and sequence analysis. Using this experimental strategy, the allelic composition of corrected and uncorrected single cells was interrogated, specifically measuring the degree of DNA heterogeneity, or onsite mutagenesis, accompanying successful and unsuccessful gene editing activity.

Figure 9A:
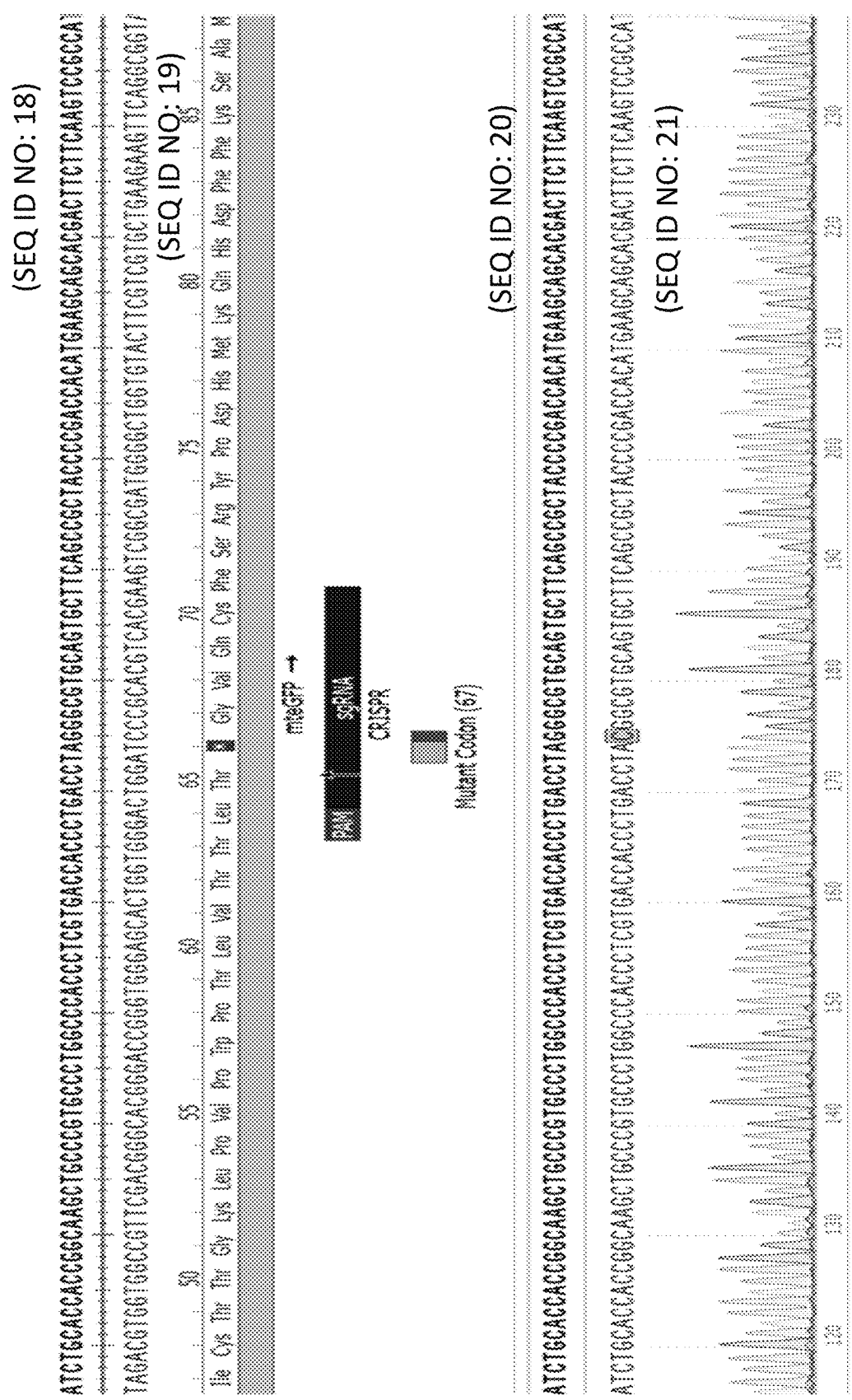
FIG. 9A illustrates allelic analysis of eGFP positive cells expanded as a clonal population. Clonally isolated and expanded eGFP positive samples (sixteen clones) were analyzed at the site surrounding the targeted base and DNA from each, harvested, purified, amplified and sequenced. Allelic analysis was carried out using Sanger sequencing, assembled using SnapGene and compared to the sequence of a wild-type allele which is illustrated at the top of the figure; the cut site of the RNP complex is indicated as a small black arrow (2C crRNA).
Figure 9B:
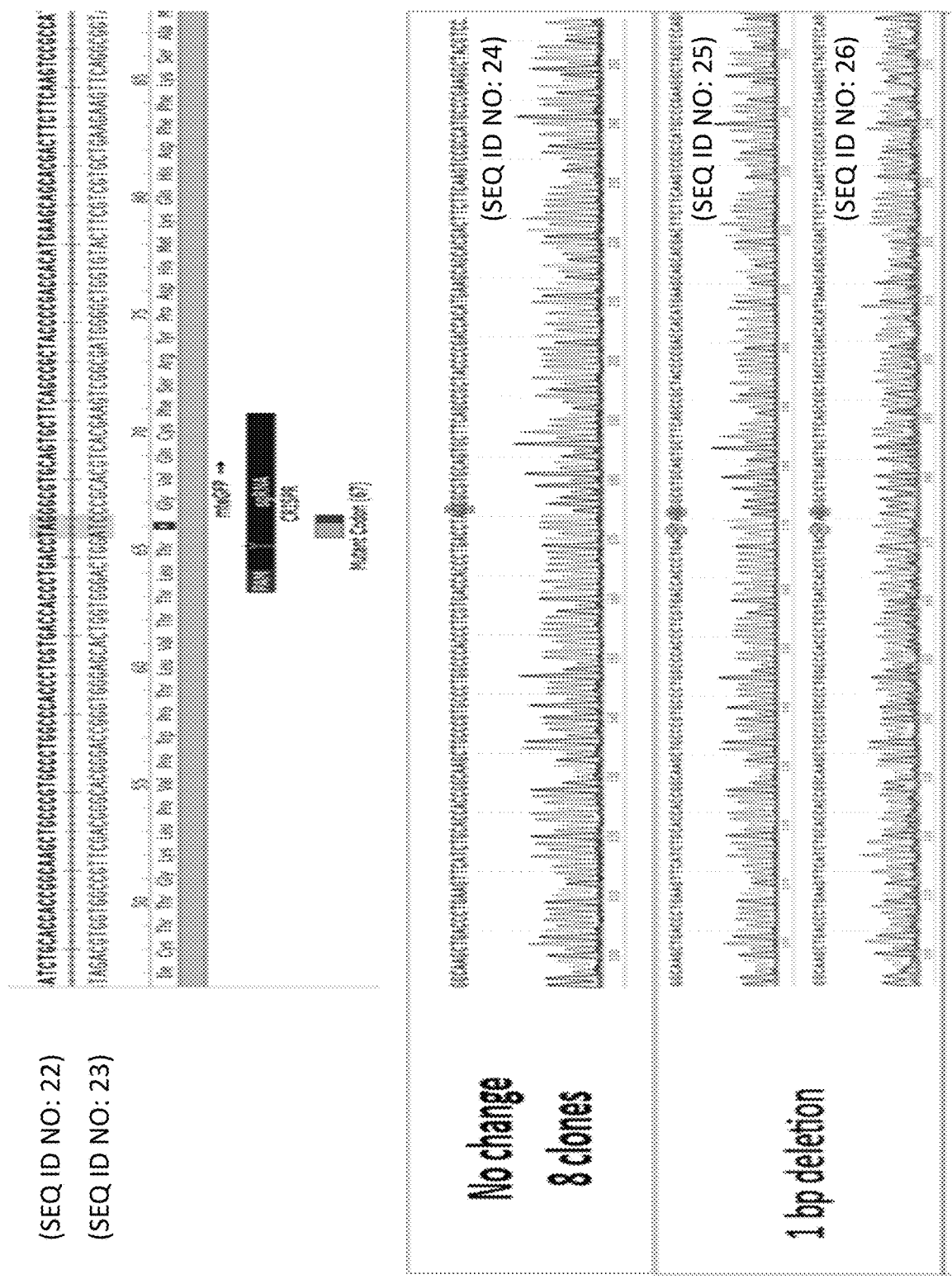
FIGS. 9B-9C illustrate allelic analysis of eGFP negative cells expanded as a clonal population. Fifteen individual samples, expanded from cloned originating from the uncorrected population were randomly selected and analyzed for indel formation at the site surrounding the target nucleotide. As above, allelic analysis was carried out using Sanger sequencing and assembled SnapGene. Once again, the sequence of a wild-type allele at the top of the figure along with the cut site of the RNP is presented.
Figure 9C:
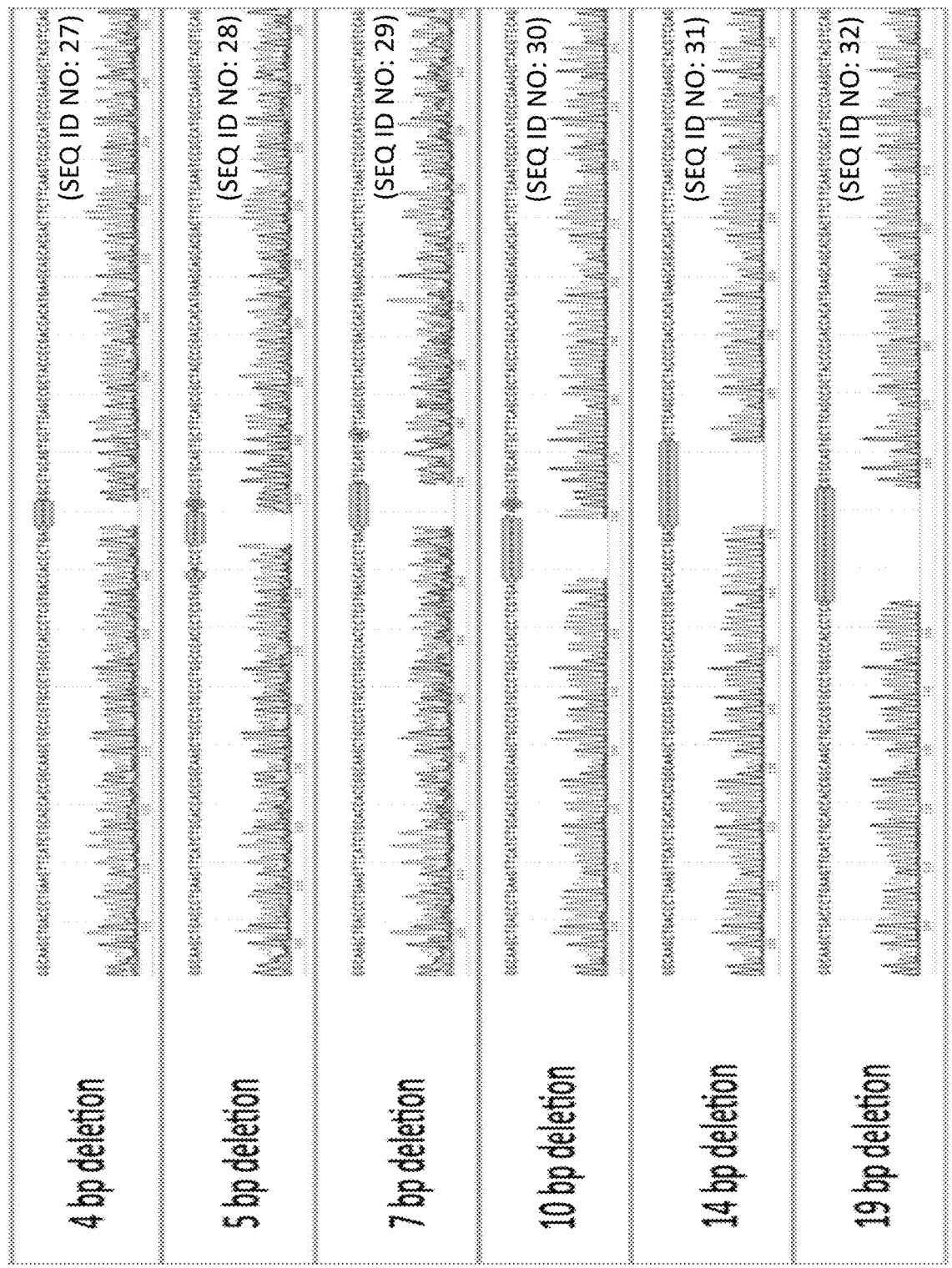
Figure 9D:
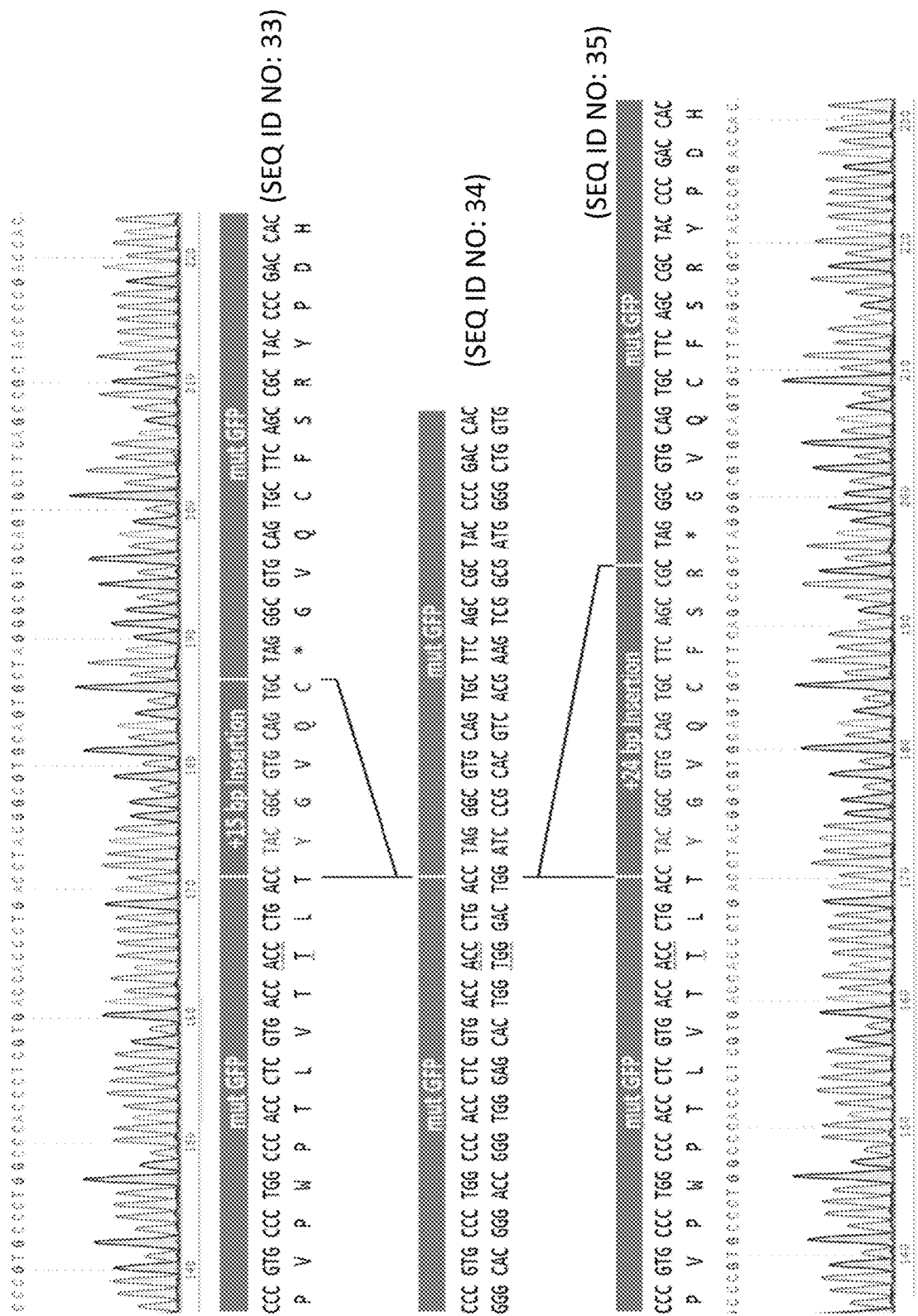
FIG. 9D illustrates allelic analysis of eGFP negative cells presenting insertions. Two individual clones from the uncorrected population displayed insertions of 15 bp (top panel) and 24 bp (bottom panel), respectively. The center panel represents the mutant eGFP gene sequence with the mutant codon depicted. The inserted bases are depicted with the corrected tyrosine codon depicted in light grey and the mutant stop codon represented by an asterisk. The boundaries of the insertions are denoted by black bars.

After sorting, isolation and expansion of corrected and uncorrected single cells, the DNA sequence of multiple clones was analyzed using direct Sanger sequencing following PCR amplification of a 718 bp long PCR fragment. As shown in FIGS. 9A-9C, precise conversion of the TAG codon, to TAC, (highlighted area) confirms phenotypic expression in the eGFP positive clones, at the DNA level. Sixteen eGFP positive clones were expanded in the same fashion and all contained the converted DNA sequence as presented in FIG. 9A. No sequence alterations or onsite mutagenesis was observed within the 718 base pair DNA region in these experiments. The DNA sequence readout found in all the clones is provided in the lower half of the figure to show that no contaminating or background sequence is present, indicating that single cell clonal expansion from the corrected population was successful. FIGS. 9B-9D illustrate the genotypic analyses of 17 eGFP-negative clonally expanded cells, selected at random from the sorted, uncorrected population. In almost half of these clones, the TAG codon remains intact and no sequence variation is observed within the region examined. In approximately half of the other clones examined on-site onsite mutagenesis consisting of both deletion and insertion mutations of varying lengths. This mutagenic activity ranged from a one base pair deletion surrounding the target site to a 19 pair deletion to a 24 base pair insertion immediately downstream from the targeted base. These results demonstrate that onsite mutagenesis occurs during RNP/ssODN gene editing reactions in cells that fail to achieve the desired phenotype.

The genotype of the two clones containing DNA insertions was examined, neither of which exhibited a change in phenotype as judged by the absence of green fluorescence. These two clones are instructive not only for what they tell about the potential for on-site mutagenesis but also what they tell about a mechanism for DNA insertion driven by single-stranded DNA. FIG. 9D displays the DNA sequence of the uncorrected clone containing a 15 base pair insertion. This insertion created a new frameshift generating the corrected TAC tyrosine codon and concomitantly created a new TAG, stop codon. Thus, this clone appears to have been corrected at the targeted base but that correction was not reflected in a phenotypic change. As such, the insertion expanded the gene by five codons. In the same fashion, a second clone containing a 24 base pair segment, inserted at the identical position, is also displayed in FIG. 9D. In this case, 8 new codons, preceding the newly created stop codon, were inserted. Thus, CRISPR/Cas9 single-stranded oligonucleotide gene editing generated a novel stretch of amino acids that are not encoded by the targeted gene. The DNA insertion matched, in perfect register, a section of the single-stranded oligonucleotide when placed in this reading frame. These data suggest that sections of the oligonucleotide can be inserted into the target gene, resulting in the simultaneous correction of the point mutation and the generation of a mutagenic footprint (see FIG. 10). The degree of mutagenesis observed in the uncorrected population is broad, signaling the importance of analyzing a representative sample of the entire population of cells targeted for genetic alteration.

Collateral mutagenesis, generated by the action the CRISPR/Cas9 gene editing tool, has been a central focus of both advocates and critics of this technology. Sophisticated molecular cloning approaches to refute, diminish or downplay the degree of off-site mutagenesis have been offered by many of the leading laboratories in the field. But, in many cases, results rely in large part on proving a negative. In fact, it is debatable as to whether or not off-site mutagenesis can be completely eliminated as a potential side reaction in therapeutic gene editing. More recently, focus has been placed on the potential of onsite mutagenesis, an outcome of the normal activity of RGENs. The inherent response of a cell to repair the double strand break through the process of non-homologous end joining is at the core of the current genetic revolution, partially inspired by RGENs, that has made the generation of gene knockouts in many eukaryotic cell types a routine lab procedure. In contrast, onsite mutagenesis becomes more relevant when the objective of the gene editing protocol is not to disable but rather to repair a gene bearing a point mutation, and eventually, to direct seamless insertion of a fragment of donor DNA.

In this study, a model system was utilized in which a mutated eGFP gene, integrated as a single copy into HCT 116 cells, was targeted for repair by the combination of a CRISPR/Cas9 RNP and a specific single-stranded DNA oligonucleotide. Successful conversion of the point mutation transformed a stop codon to a tyrosine codon enabling translation and expression of functional eGFP. Because the cells were cloned and examined as uniquely expanded populations, allelic analysis of gene editing activity in both corrected and uncorrected populations was possible. The combination of the RNP complex and a 72-mer directed gene repair of the point mutation in an efficient and reproducible fashion. Keeping the molecular ratio of the RNP and the single-strand DNA oligonucleotide constant but raising the total amount in the reaction induced a dose-dependent response which began to plateau above 10%; at an 8 to 10 fold higher level than when the ssODN was used as the sole gene editing agent. All of the appropriate reaction components were required for successful point mutation repair and the separation of the corrected and uncorrected cells could be achieved in a straightforward fashion. Without wishing to be limited by any theory, the rationale for using the RNP was that the active components of the CRISPR/Cas9 system were delivered to the nucleus at approximately the same time facilitating a more constant initialization of the gene editing reaction. Point mutation repair driven by the combination of the RNP and the ssODN was confirmed in the study.

With regard to the examination of DNA heterogeneity in corrected and uncorrected populations, cells identified by FACS as being corrected, exhibited precise single base repair at the target site. No genetic alterations were observed with cells from the corrected population for a proximal distance of 718 bases. In addition, no nucleotide changes were observed that would result in a conservative change in amino acid sequence still enabling expression of alternative wild type eGFP.

The clonal expansion of a population of cells that did not exhibit phenotypic correction generated a panel of genetic alterations ranging from uncorrected, yet intact, to a cell line bearing a 19 base deletion surrounding the target site to the insertion of 24 bases surrounding the target site respectively. Of the 17 clones tested, eight had no change to the mutant DNA sequence, perhaps indicating that the RNP complex had not reached the target site in those cells, had not induced by double strand break at the site, or had induced a double strand break which was properly and efficiently repaired with or without the aid of the single-stranded oligonucleotide. A wide range of DNA sequence deletions were observed starting with a single base deletion and ending with a 19 base deletion, heterogeneity that surrounds the nucleotide targeted for gene repair. No other sequence alterations outside of the target site were observed, again within the proximal 718 bases. The one clone harboring a 15 base insertion, appeared to arise through a duplication of the adjacent 15 bases located 5' to the target site, as well as a 24 base insertion that appears to have come from the same DNA source. These results indicate that onsite mutagenesis clearly occurs in the uncorrected population of cells, exhibiting a wide range of indel formation.

Figure 10:
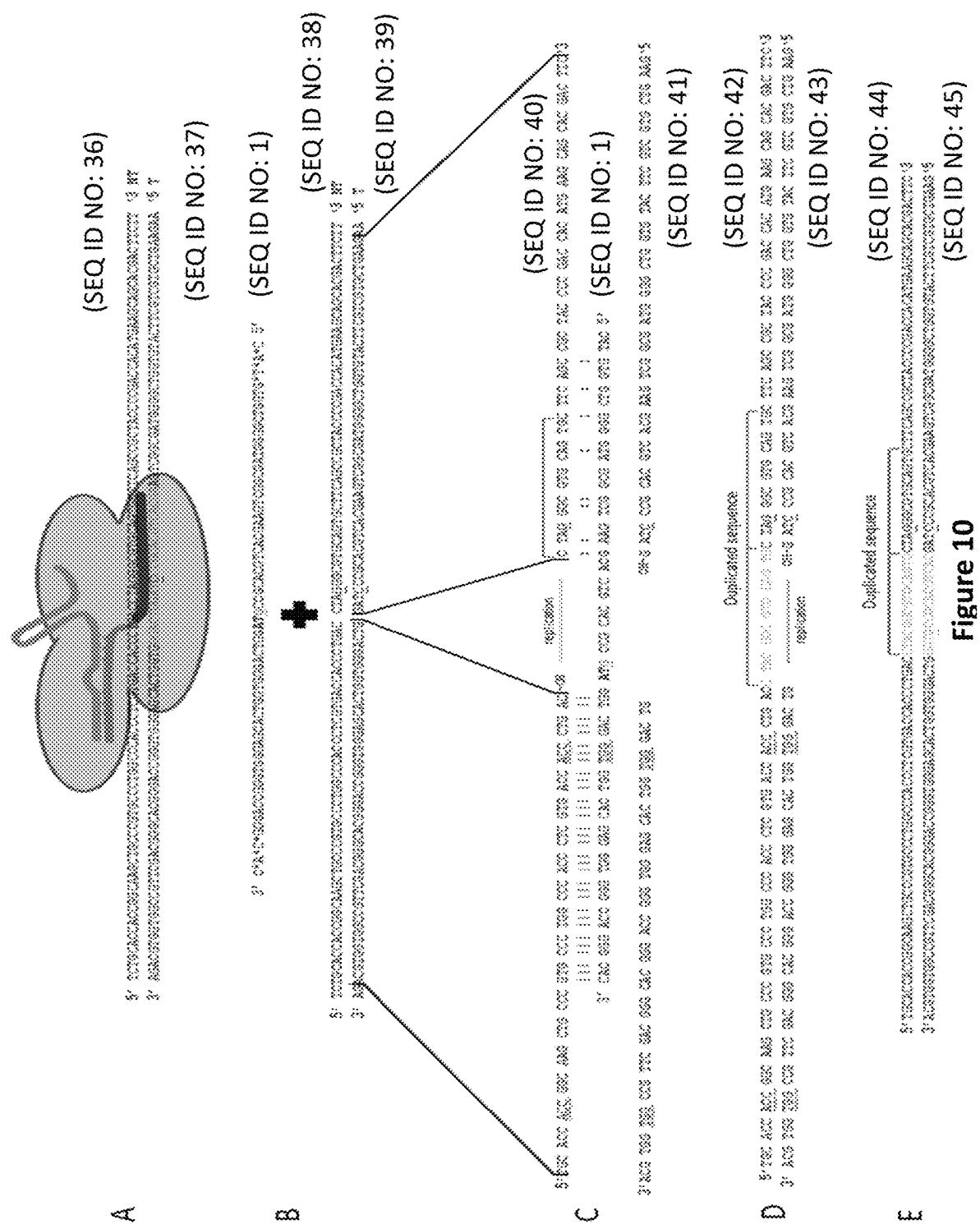
FIG. 10 illustrates a model for point mutation repair directed by an RNP complex and a short single-stranded DNA oligonucleotide. Panels A and B: the RNP particle induces a double strand break at the target site generating two free 3' hydroxyl ends on each strand of the broken DNA. Panel C: the oligonucleotide aligns in imperfect homologous register with the non-transcribed strand of the chromosome. The DNA replication machinery fills the gap starting from the 3'-hydroxyl end and completing by ligation to the 5'-phosphate at the opposite side of the gap. The single-stranded oligonucleotide serves as a template for the replication process. Panels D/E: dissociation of the single-stranded oligonucleotide allows for the newly synthesized DNA to act as a template for DNA replication in the opposite direction on the bottom strand followed by ligation.

No homologous recombination events from distal sites were observed, wherein genetic information was provided by adjacent chromosomes to aid in the repair of the fragmented DNA. The DNA sequence of the insertion clones, however, enabled a continuation of the reading frame through several codons until a stop codon was generated so additional genetic information was proved in some fashion. Both insertion clones contained the exact corrected point mutation but did not score as eGFP+ because the inserted DNA created a stop codon 15 or 24 bases downstream from the targeted nucleotide respectively. This is an interesting example of how double strand DNA breakage can provide a site for DNA insertion of exogenous or repetitive segments as the cell responds to chromosomal damage. These data provide insight into the overall mechanism by which short oligonucleotides and the RNP execute the repair of a point mutation in a mammalian cell. FIG. 10 displays a model that explains the generation of cells bearing only a corrected genotype, as well as cells bearing both corrected genotype and phenotype.

The model described in the present study is based on the well-accepted and standard model Double Strand Break Repair. When a double strand break occurs in a mammalian chromosome (in the case of gene editing, induced by CRISPR/Cas9 activity), activated exonucleases recognize the break and resect the broken ends to varying degrees, a biochemical reaction that takes place regardless of whether the break is designated for repair through the process of homologous recombination or nonhomologous end joining. In the case of homologous recombination however, usually occurring during S-phase of the cell cycle, proteins involved in DNA recombinational repair load onto the broken ends. Subsequently, a sister chromatid provides the DNA template to enable the broken strand to once again be made whole through the process of gap filling by DNA replication. Since crossover of one strand of DNA from the sister chromatin provides the template, its original partner strand is displaced and becomes the template for gap filling through DNA replication, albeit in the opposite polarity. Thus, the gap created by the original double strand break is repaired through the utilization of an exogenous piece of DNA that serves as a source of genetic information and the template for replication activity and gap filling. This general concept can help explain the appearance of these two insertional mutants and may also explain previous data including the overall reaction of how single-stranded oligonucleotides direct point mutation repair in mammalian cells.

The RNP particle, as illustrated in FIG. 10, Panel A, interacts at the target site and catalyzes a double strand break leaving two 3' hydroxyl ends available for extension by the DNA replication machinery. Non-homologous end joining activity resects the broken ends and the degree of this resection varies from clone to clone (FIG. 10, Panel B). The clones expanded from the uncorrected population support the fact that varying degrees of resection take place (see FIGS. 9B-9C) because DNA insertions of 15 and 24 bases were found. As illustrated in FIG. 10, Panel C, the oligonucleotide (red) pairs stably with the target gene via sequence complementarity, bridging the gap in the top strand. The binding is more stable upstream since the ssODN aligns in homologous register using perfect complementarity. Downstream from the break site, the base pairing must be incomplete because the data reveals a duplication of adjacent sequences. The partial binding downstream from the resected site is, in fact, energetically favorable based on calculations of free energy (approximately $\Delta G$ of $-2.6$). The oligonucleotide has been designed to be complementary to the non-transcribed strand and thus the polarity of pairing partners can be depicted with confidence. As illustrated in FIG. 10, Panel D and as a result of resection, a free 3' hydroxyl end on the top strand is now available for extension by DNA replication. In this simple model, the oligonucleotide acts as a template for the replication machinery to fill in the gap in the upper strand. For these two clones, the single-stranded oligonucleotide used in the gene editing reaction contains a G residue at its center because it is designed to create a single base mismatch with the G residue in the gene and promote mismatch repair. This strategy is based on work on single agent gene editing wherein the objective is not DNA insertion but rather nucleotide exchange through the process of mismatch repair or by incorporation of the oligonucleotide into a growing replication fork. In contrast to some other models of gene editing, sequencing data indicate that the oligonucleotide itself does not insert directly because, if this had happened, then the base at that position, identified in the genomic sequence (FIG. 9D), would have been a G, not a C. After serving as a template for replication, the oligonucleotide dissociates (FIG. 10, Panel D) and DNA replication is initiated on the opposite strand and in the opposite direction by utilizing the free hydroxyl group for extension as illustrated in FIG. 10, Panel E. This variant of gene editing was termed 'EXACT' for EXcision And Corrective Therapy; it may also be the general mechanism by which point mutations are repaired in gene editing reactions as directed by short oligonucleotides and double strand DNA breaks at the target site.

Importantly, fragment insertion for point mutation repair was not observed because none of the clones examined in this study contained the G nucleotide at the target site. Since double strand DNA breaks are widely recognized as being both dangerous to cell viability and highly recombinogenic, it is likely that multiple pathways are used to regenerate a contiguous chromosome. The mechanism of repair may be dictated by the type and structure of donor DNA available at the site of damage.

The disclosures of each and every patent, patent application, and publication cited herein are hereby incorporated herein by reference in their entirety.

While the invention has been disclosed with reference to specific embodiments, it is apparent that others skilled in the art may devise other embodiments and variations of this invention without departing from the true spirit and scope of the invention. The appended claims are intended to be construed to include all such embodiments and equivalent variations.

What is claimed is:

1. A method of exchanging a single nucleotide in a DNA sequence using a CRISPR/Cas9 system in a synchronized and released population of cells in vitro, the method comprising:

cleaving a DNA within 20 bases of a single nucleotide target site in the synchronized and released population of cells using at least one CRISPR/Cas9 system comprising a ribonucleoprotein (RNP) complex, thereby generating a cleaved DNA comprising a first cleavage end and a second cleavage end;

exchanging a single nucleotide at the single nucleotide target site by (a) annealing the cleaved DNA with a single-stranded deoxyoligonucleotide about 72 nucleotides in length comprising (i) a first region 100% complementary to the first cleavage end and at least one deoxynucleotide adjacent to the first cleavage end of the cleaved DNA, (ii) a second region 100% complementary to the second cleavage end and at least one deoxynucleotide adjacent to the second cleavage end of the cleaved DNA, and (iii) a single mismatched nucleotide as compared to the single nucleotide target site of the DNA and (b) fusing the first and second cleavage ends of the cleaved DNA with no insertion and deletion of one or more unwanted deoxynucleotides at the junction of the first and second cleavage ends of the cleaved DNA to generate a repaired DNA at the single nucleotide target site comprising a repaired nucleotide complementary to the single mismatched nucleotide of the single-stranded deoxyoligonucleotide.

2. The method of claim 1, wherein the first region of the single-stranded deoxyoligonucleotide is directly linked to the second region of the single-stranded deoxyoligonucleotide.

3. A method of exchanging a single nucleotide in a DNA sequence cleaved by a CRISPR/Cas9 system in a synchronized and released population of cells in vitro, the method comprising:

exchanging a single nucleotide at a single nucleotide target site that is within 20 bases of the CRISPR/Cas9 cleavage site without introducing an insertion or deletion of one or more unwanted deoxynucleotides by (a) annealing a single-stranded oligonucleotide about 72 nucleotides in length to a DNA cleaved in one or more sites using at least one CRISPR/Cas9 system comprising a ribonucleoprotein (RNP) complex in the synchronized and released population of cells and (b) fusing a first cleavage end and a second cleavage ends of the cleaved DNA with no insertion and deletion of one or more unwanted deoxynucleotides at the junction of the first and second cleavage ends of the cleaved DNA to generate a repaired DNA comprising a repaired nucleotide complementary to the single mismatched nucleotide of the single-stranded deoxyoligonucleotide, wherein the single-stranded oligonucleotide comprises (i) a first region 100% complementary to the first cleavage end and at least one deoxynucleotide adjacent to the first cleavage end of the cleaved DNA, (ii) a second region 100% complementary to the second cleavage end and at least one deoxynucleotide adjacent to the second cleavage end of the cleaved DNA, and (iii) a single mismatched nucleotide as compared to the single nucleotide target site of the DNA.

4. The method of claim 3, wherein the one or more unwanted insertion or deletion is selected from the group consisting of: a single deoxynucleotide, and two or more deoxynucleotides.

5. The method of claim 3, wherein the at least one deoxynucleotide adjacent to the first cleavage end and the at least one deoxynucleotide adjacent to the second generated cleavage end independently comprise about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60 deoxynucleotides.

6. The method of claim 3, wherein the first region of the single-stranded oligonucleotide is directly linked to the second region of the single-stranded oligonucleotide.

7. The method of claim 1, wherein no collateral on-site or off-site DNA mutagenesis is produced.

8. The method of claim 3, wherein no collateral on-site or off-site DNA mutagenesis is produced.

* * * * *

SEQUENCE LISTING

```
<160> NUMBER OF SEQ ID NOS: 45

<210> SEQ ID NO 1
<211> LENGTH: 72
<212> TYPE: DNA
<213> ORGANISM: Artificial Sequence
<220> FEATURE:
<223> OTHER INFORMATION: oligonucleotide

<400> SEQUENCE: 1
catgtggtcg gggtagcggc tgaagcactg cacgccgtag gtcagggtgg tcacgagggt      60
gggccagggc ac                                                         72

<210> SEQ ID NO 2
<211> LENGTH: 72
<212> TYPE: DNA
<213> ORGANISM: Artificial Sequence
<220> FEATURE:
<223> OTHER INFORMATION: Partial reporter gene sequence

<400> SEQUENCE: 2
gtgccctggc ccaccctcgt gaccaccctg acctacggcg tgcagtgctt cagccgctac      60
cccgaccaca tg                                                         72

<210> SEQ ID NO 3
<211> LENGTH: 72
<212> TYPE: DNA
<213> ORGANISM: Artificial Sequence
<220> FEATURE:
<223> OTHER INFORMATION: Partial reporter gene sequence

<400> SEQUENCE: 3
gtgccctggc ccaccctcgt gaccaccctg acctagggcg tgcagtgctt cagccgctac      60
cccgaccaca tg                                                         72

<210> SEQ ID NO 4
<211> LENGTH: 21
<212> TYPE: DNA
```

```
<213> ORGANISM: Artificial sequence
<220> FEATURE:
<223> OTHER INFORMATION: primer

<400> SEQUENCE: 4
ctggacggcg acgtaaacgg c                                              21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
accatgtgat cgcgcttctc g                                              21

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
tcctaagcca gtgccagaag ag                                             22

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ctattggtct ccttaaacct                                                20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
atggtgagca agggcgagga                                                20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
acttgtacag ctcgtccatg c                                              21

<210> SEQ ID NO 10
<211> LENGTH: 112
<212> TYPE: DNA
<213> ORGANISM: Artificial Sequence
<220> FEATURE:
<223> OTHER INFORMATION: Partial reporter gene sequence

<400> SEQUENCE: 10
tctgcaccac cggcaagctg cccgtgccct ggcccaccct cgtgaccacc ctgacctagg    60
```

```
gcgtgcagtg cttcagccgc taccccgacc acatgaagca gcacgacttc tt          112
```

<210> SEQ ID NO 11
<211> LENGTH: 112
<212> TYPE: DNA
<213> ORGANISM: Artificial Sequence
<220> FEATURE:
<223> OTHER INFORMATION: Partial reporter gene sequence

<400> SEQUENCE: 11

```
aagaagtcgt gctgcttcat gtggtcgggg tagcggctga agcactgcac gccctaggtc    60
agggtggtca cgagggtggg ccagggcacg ggcagcttgc cggtggtgca ga           112
```

<210> SEQ ID NO 12
<211> LENGTH: 112
<212> TYPE: DNA
<213> ORGANISM: Artificial Sequence
<220> FEATURE:
<223> OTHER INFORMATION: Partial reporter gene sequence

<400> SEQUENCE: 12

```
tctgcaccac cggcaagctg cccgtgccct ggcccaccct cgtgaccacc ctgacctacg    60
gcgtgcagtg cttcagccgc taccccgacc acatgaagca gcacgacttc tt           112
```

<210> SEQ ID NO 13
<211> LENGTH: 112
<212> TYPE: DNA
<213> ORGANISM: Artificial Sequence
<220> FEATURE:
<223> OTHER INFORMATION: Partial reporter gene sequence

<400> SEQUENCE: 13

```
aagaagtcgt gctgcttcat gtggtcgggg tagcggctga agcactgcac gccgtaggtc    60
agggtggtca cgagggtggg ccagggcacg ggcagcttgc cggtggtgca ga           112
```

<210> SEQ ID NO 14
<211> LENGTH: 20
<212> TYPE: DNA
<213> ORGANISM: Artificial Sequence
<220> FEATURE:
<223> OTHER INFORMATION: protospacer

<400> SEQUENCE: 14

```
agcactgcac gccctaggtc                                                20
```

<210> SEQ ID NO 15
<211> LENGTH: 20
<212> TYPE: DNA
<213> ORGANISM: Artificial Sequence
<220> FEATURE:
<223> OTHER INFORMATION: crRNA

<400> SEQUENCE: 15

```
agcactgcac gccctaggtc                                                20
```

<210> SEQ ID NO 16
<211> LENGTH: 87
<212> TYPE: DNA
<213> ORGANISM: Artificial Sequence
<220> FEATURE:
<223> OTHER INFORMATION: tracrRNA

<400> SEQUENCE: 16
gttggaacca ttcaaaacag catagcaagt taaaataagg ctagtccgtt atcaacttga     60
aaaagtggca ccgagtcggt gcttttt                                        87

<210> SEQ ID NO 17
<211> LENGTH: 72
<212> TYPE: DNA
<213> ORGANISM: Artificial Sequence
<220> FEATURE:
<223> OTHER INFORMATION: Partial reporter gene sequence

<400> SEQUENCE: 17
catgtggtcg gggtagcggc tgaagcactg cacgccctag gtcagggtgg tcacgagggt     60
gggccagggc ac                                                        72

<210> SEQ ID NO 18
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 18
acttgcacca ccggcaagct gcccgtgccc tggcccaccc tcgtgaccac cctgacctag     60
ggcgtgcagt gcttcagccg ctaccccgac cacatgaagc agcacgactt cttcaagtcc    120
gcca                                                                124

<210> SEQ ID NO 19
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 19
tggcggactt gaagaagtcg tgctgcttca tgtggtcggg gtagcggctg aagcactgca     60
cgccctaggt cagggtggtc acgagggtgg gccagggcac gggcagcttg ccggtggtgc    120
agat                                                                124

<210> SEQ ID NO 20
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 20
atctgcacca ccggcaagct gcccgtgccc tggcccaccc tggtgaccac cctgacctag     60
ggcgtgcagt gcttcagccg ctaccccgac cacatgaagc agcacgactt cttcaagtcc    120
gcca                                                                124

<210> SEQ ID NO 21
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 21
accgcctgaa cttcttcagc acgacgaagt acaccagccc catcgccgac ttcgtgacgt     60
gcggcatcca gtcccaccag tgctcccacc cggtcccgtg cccgtcgaac ggccaccacg    120

```
<210> SEQ ID NO 22
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 22
atctgcacca ccggcaagct gcccgtgccc tggcccaccc tcgtgaccac cctgacctag    60
ggcgtgcagt gcttcagccg ctaccccgac cacatgaagc agcacgactt cttcaagtcc   120
gcca                                                                124

<210> SEQ ID NO 23
<211> LENGTH: 124
<212> TYPE: DNA
<213> ORGANISM: Artificial Sequence
<220> FEATURE:
<223> OTHER INFORMATION: Partial reporter gene sequence

<400> SEQUENCE: 23
tggcggactt gaagaagtcg tgctgcttca tgtggtcggg gtagcggctg aagcactgca    60
cgccctaggt cagggtggtc acgagggtgg gccagggcac gggcagcttg ccggtggtgc   120
agat                                                                124

<210> SEQ ID NO 24
<211> LENGTH: 163
<212> TYPE: DNA
<213> ORGANISM: Artificial Sequence
<220> FEATURE:
<223> OTHER INFORMATION: Partial reporter gene sequence

<400> SEQUENCE: 24
ggcaagctga ccctgaagtt catctgcacc accggcaagc tgcccgtgcc ctggcccacc    60
ctcgtgacca ccctgaccta gggcgtgcag tgcttcagcc gctaccccga ccacatgaag   120
cagcacgact tcttcaagtc cgccatgccc gaaggctacg tcc                     163

<210> SEQ ID NO 25
<211> LENGTH: 164
<212> TYPE: DNA
<213> ORGANISM: Artificial Sequence
<220> FEATURE:
<223> OTHER INFORMATION: Partial reporter gene sequence

<400> SEQUENCE: 25
ggcaagctga ccctgaagtt catctgcacc accggcaagc tgcccgtgcc ctggcccacc    60
ctcgtgacca ccctgactag ggcgtgcagt gcttcagccg ctaccccgac cacatgaagc   120
agcacgactt cttcaagtcc gccatgcccg aaggctacgt ccag                    164

<210> SEQ ID NO 26
<211> LENGTH: 164
<212> TYPE: DNA
<213> ORGANISM: Artificial Sequence
<220> FEATURE:
<223> OTHER INFORMATION: Partial reporter gene sequence

<400> SEQUENCE: 26
ggcaagctga ccctgaagtt catctgcacc accggcaagc tgcccgtgcc ctggcccacc    60
```

```
ctcgtgacca ccctgactac ggcgtgcagt gcttcagccg ctaccccgac cacatgaagc    120
agcacgactt cttcaagtcc gccatgcccg aaggctacgt ccag                     164
```

<210> SEQ ID NO 27
<211> LENGTH: 161
<212> TYPE: DNA
<213> ORGANISM: Artificial Sequence
<220> FEATURE:
<223> OTHER INFORMATION: Partial reporter gene sequence

<400> SEQUENCE: 27

```
ggcaagctga ccctgaagtt catctgcacc accggcaagc tgcccgtgcc ctggcccacc     60
ctcgtgacca ccctgacggc gtgcagtgct tcagccgcta ccccgaccac atgaagcagc    120
acgacttctt caagtccgcc atgcccgaag gctacgtcca g                        161
```

<210> SEQ ID NO 28
<211> LENGTH: 159
<212> TYPE: DNA
<213> ORGANISM: Artificial Sequence
<220> FEATURE:
<223> OTHER INFORMATION: Partial reporter gene sequence

<400> SEQUENCE: 28

```
ggcaagctga ccctgaagtt catctgcacc accggcaagc tgcccgtgcc ctggcccacc     60
ctcgtgacac cctagggcgt gcagtgcttc agccgctacc ccgaccacat gaagcagcac    120
gacttcttca gtccgccat gcccgaaggc tacgtccag                            159
```

<210> SEQ ID NO 29
<211> LENGTH: 158
<212> TYPE: DNA
<213> ORGANISM: Artificial Sequence
<220> FEATURE:
<223> OTHER INFORMATION: Partial reporter gene sequence

<400> SEQUENCE: 29

```
ggcaagctga ccctgaagtt catctgcacc accggcaagc tgcccgtgcc ctggcccacc     60
ctcgtgacca ccctgacgtg cagtgattca gccgctaccc cgaccacatg aagcagcacg    120
acttcttcaa gtccgccatg cccgaaggct acgtccag                            158
```

<210> SEQ ID NO 30
<211> LENGTH: 155
<212> TYPE: DNA
<213> ORGANISM: Artificial Sequence
<220> FEATURE:
<223> OTHER INFORMATION: Partial reporter gene sequence

<400> SEQUENCE: 30

```
ggcaagctga ccctgaagtt catctgcacc accggcaagc tgcccgtgcc ctggcccacc     60
ctcgtgacta gggcgtgcag tgcttcagcc gctaccccga ccacatgaag cagcacgact    120
tcttcaagtc cgccatgccc gaaggctacg tccag                               155
```

<210> SEQ ID NO 31
<211> LENGTH: 151
<212> TYPE: DNA
<213> ORGANISM: Artificial Sequence
<220> FEATURE:
<223> OTHER INFORMATION: Partial reporter gene sequence

<400> SEQUENCE: 31

```
ggcaagctga ccctgaagtt catctgcacc accggcaagc tgcccgtgcc ctggcccacc     60
```

```
ctcgtgacca ccctgacgct tcagccgcta ccccgaccac atgaagcagc acgacttctt    120
caagtccgcc atgcccgaag gctacgtcca g                                   151

<210> SEQ ID NO 32
<211> LENGTH: 146
<212> TYPE: DNA
<213> ORGANISM: Artificial Sequence
<220> FEATURE:
<223> OTHER INFORMATION: Partial reporter gene sequence

<400> SEQUENCE: 32
ggcaagctga ccctgaagtt catctgcacc accggcaagc tgcccgtgcc ctggcccacc    60
ctcgcgtgca gtgcttcagc cgctaccccg accacatgaa gcagcacgac ttcttcaagt    120
ccgccatgcc cgaaggctac gtccag                                         146

<210> SEQ ID NO 33
<211> LENGTH: 87
<212> TYPE: DNA
<213> ORGANISM: Artificial Sequence
<220> FEATURE:
<223> OTHER INFORMATION: Partial reporter gene sequence

<400> SEQUENCE: 33
cccgtgccct ggcccaccct cgtgaccacc ctgacctacg gcgtgcagtg ctagggcgtg    60
cagtgcttca gccgctaccc cgaccac                                        87

<210> SEQ ID NO 34
<211> LENGTH: 72
<212> TYPE: DNA
<213> ORGANISM: Artificial Sequence
<220> FEATURE:
<223> OTHER INFORMATION: Partial reporter gene sequence

<400> SEQUENCE: 34
cccgtgccct ggcccaccct cgtgaccacc ctgacctagg gcgtgcagtg cttcagccgc    60
taccccgacc ac                                                        72

<210> SEQ ID NO 35
<211> LENGTH: 96
<212> TYPE: DNA
<213> ORGANISM: Artificial Sequence
<220> FEATURE:
<223> OTHER INFORMATION: Partial reporter gene sequence

<400> SEQUENCE: 35
cccgtgccct ggcccaccct cgtgaccacc ctgacctacg gcgtgcagtg cttcagccgc    60
tagggcgtgc agtgcttcag ccgctacccc gaccac                              96

<210> SEQ ID NO 36
<211> LENGTH: 101
<212> TYPE: DNA
<213> ORGANISM: Artificial Sequence
<220> FEATURE:
<223> OTHER INFORMATION: Artificially generated sequence

<400> SEQUENCE: 36
tctgcaccac cggcaagctg cccgtgccct ggcccaccct gaccttaggg cgtgcagtgc    60
ttcagccgct accccgacca catgaagcag cacgacttct t                        101

<210> SEQ ID NO 37
```

```
<211> LENGTH: 112
<212> TYPE: DNA
<213> ORGANISM: Artificial Sequence
<220> FEATURE:
<223> OTHER INFORMATION: Artificially generated sequence

<400> SEQUENCE: 37
aagaagtcgt gctgcttcat gtggtcgggg tagcggctga agcactgcac gccctaggtc      60
agggtggtca cgagggtggg ccagggcagc ggcagcttgc cggtggtgca ga             112

<210> SEQ ID NO 38
<211> LENGTH: 112
<212> TYPE: DNA
<213> ORGANISM: Artificial Sequence
<220> FEATURE:
<223> OTHER INFORMATION: Artificially generated sequence

<400> SEQUENCE: 38
tctgcaccac cggcaagctg cccgtgccct ggcccaccct cgtgaccacc ctgacctagg      60
gcgtgcagtg cttcagccgc taccccgacc acatgaagca gcacgacttc tt             112

<210> SEQ ID NO 39
<211> LENGTH: 112
<212> TYPE: DNA
<213> ORGANISM: Artificial Sequence
<220> FEATURE:
<223> OTHER INFORMATION: Artificially generated sequence

<400> SEQUENCE: 39
aagaagtcgt gctgcttcat gtggtcgggg tagcggctga agcactgcac gccctaggtc      60
agggtggtca cgagggtggg ccagggcacg ggcagcttgc cggtggtgca ga             112

<210> SEQ ID NO 40
<211> LENGTH: 108
<212> TYPE: DNA
<213> ORGANISM: Artificial Sequence
<220> FEATURE:
<223> OTHER INFORMATION: Artificially generated sequence

<400> SEQUENCE: 40
tgcaccaccg gcaagctgcc cgtgccctgg cccaccctcg tgaccaccct gacctaggtc      60
gtgcagtgct tcagccgcta ccccgaccac atgaagcagc acgacttc                  108

<210> SEQ ID NO 41
<211> LENGTH: 108
<212> TYPE: DNA
<213> ORGANISM: Artificial Sequence
<220> FEATURE:
<223> OTHER INFORMATION: Artificially generated sequence

<400> SEQUENCE: 41
gaagtcgtgc tgcttcatgt ggtcgggta gcggctgaag cactgcacgc cctaggtcag      60
ggtggtcacg agggtgggcc agggcacggg cagcttgccg gtggtgca                 108

<210> SEQ ID NO 42
<211> LENGTH: 123
<212> TYPE: DNA
<213> ORGANISM: Artificial Sequence
<220> FEATURE:
<223> OTHER INFORMATION: Artificially generated sequence

<400> SEQUENCE: 42
tgcaccaccg gcaagctgcc cgtgccctgg cccaccctcg tgaccaccct gacctacggc     60
```

```
<210> SEQ ID NO 43
<211> LENGTH: 108
<212> TYPE: DNA
<213> ORGANISM: Artificial Sequence
<220> FEATURE:
<223> OTHER INFORMATION: Artificially generated sequence

<400> SEQUENCE: 43
gaagtcgtgc tgcttcatgt ggtcggggta gcggctgaag cactgcacgc cctaggtcag      60
ggtggtcacg agggtgggcc agggcacggg cagcttgccg gtggtgca                 108

<210> SEQ ID NO 44
<211> LENGTH: 123
<212> TYPE: DNA
<213> ORGANISM: Artificial Sequence
<220> FEATURE:
<223> OTHER INFORMATION: Artificially generated sequence

<400> SEQUENCE: 44
tgcaccaccg gcaagctgcc cgtgccctgg cccaccctcg tgaccaccct gacctacggc      60
gtgcagtgct agggcgtgca gtgcttcagc cgctaccccg accacatgaa gcagcacgac     120
ttc                                                                  123

<210> SEQ ID NO 45
<211> LENGTH: 123
<212> TYPE: DNA
<213> ORGANISM: Artificial Sequence
<220> FEATURE:
<223> OTHER INFORMATION: Artificially generated sequence

<400> SEQUENCE: 45
gaagtcgtgc tgcttcatgt ggtcggggta gcggctgaag cactgcacgc cctagcactg      60
cacgccgtag gtcagggtgg tcacgagggt gggccagggc acgggcagct tgccggtggt     120
gca                                                                  123
```